(12) United States Patent
Keefe et al.

(10) Patent No.: US 10,738,123 B2
(45) Date of Patent: Aug. 11, 2020

(54) ANTI-FLT-1 ANTIBODIES IN TREATING BRONCHOPULMONARY DYSPLASIA

(71) Applicants: SHIRE HUMAN GENETIC THERAPIES, INC., Lexington, MA (US); THE REGENTS OF THE UNIVERSITY OF COLORADO, A BODY CORPORATE, Denver, CO (US)

(72) Inventors: Dennis Keefe, Lexington, MA (US); Steven Abman, Aurora, CO (US); Gregory Seedorf, Aurora, CO (US)

(73) Assignees: Shire Human Genetic Therapies, Inc., Lexington, MA (US); The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 15/564,969

(22) PCT Filed: Apr. 7, 2016

(86) PCT No.: PCT/US2016/026420
§ 371 (c)(1),
(2) Date: Feb. 7, 2018

(87) PCT Pub. No.: WO2016/164567
PCT Pub. Date: Oct. 13, 2016

(65) Prior Publication Data
US 2018/0072805 A1    Mar. 15, 2018

Related U.S. Application Data

(60) Provisional application No. 62/144,241, filed on Apr. 7, 2015.

(51) Int. Cl.
| | |
|---|---|
| C07K 16/28 | (2006.01) |
| A61K 9/00 | (2006.01) |
| A61K 39/00 | (2006.01) |
| A23L 33/10 | (2016.01) |
| A61K 31/07 | (2006.01) |
| A61K 31/56 | (2006.01) |
| A61K 33/00 | (2006.01) |
| A61K 39/395 | (2006.01) |
| A61K 45/06 | (2006.01) |

(52) U.S. Cl.
CPC .......... C07K 16/2863 (2013.01); A23L 33/10 (2016.08); A61K 9/007 (2013.01); A61K 9/0012 (2013.01); A61K 9/0019 (2013.01); A61K 9/0053 (2013.01); A61K 9/0073 (2013.01); A61K 31/07 (2013.01); A61K 31/56 (2013.01); A61K 33/00 (2013.01); A61K 39/3955 (2013.01); A61K 45/06 (2013.01); A23V 2002/00 (2013.01); A61K 2039/505 (2013.01); A61K 2039/54 (2013.01); A61K 2039/545 (2013.01); C07K 2317/21 (2013.01); C07K 2317/24 (2013.01); C07K 2317/33 (2013.01); C07K 2317/52 (2013.01); C07K 2317/54 (2013.01); C07K 2317/55 (2013.01); C07K 2317/622 (2013.01); C07K 2317/626 (2013.01); C07K 2317/74 (2013.01); C07K 2317/76 (2013.01); C07K 2317/92 (2013.01); C07K 2317/94 (2013.01)

(58) Field of Classification Search
CPC ............ C07K 16/2863; C07K 2317/52; C07K 2317/76; A61K 9/007; A61K 9/0019; A61K 2039/505; A61K 2039/54; A61K 2039/545
See application file for complete search history.

(56) References Cited

U.S. PATENT DOCUMENTS

7,335,362 B2 * 2/2008 Karumanchi ........ A61K 31/522
424/198.1

FOREIGN PATENT DOCUMENTS

| WO | WO2004/008946 A2 | 1/2004 |
|---|---|---|
| WO | WO2006/055809 A2 | 5/2006 |
| WO | WO2006/076467 A2 | 7/2006 |
| WO | WO2010/075475 A1 | 7/2010 |
| WO | WO2012/109282 A2 | 8/2012 |
| WO | WO2014/117160 A1 | 7/2014 |
| WO | WO2014/150314 A1 | 9/2014 |

OTHER PUBLICATIONS

Tang et al., Excess soluble vascular endothelial growth factor receptor-1 in amniotic fluid impairs lung growth in rats: linking preeclampsia with bronchopulmonary dysplasia. Am J Physiol Lung Cell Mol Physiol. 302(1):L36-46, 2012.*
Ennen, J. P. et al., "Vascular-targeted therapies for Duchene muscular dystrophy", Skeletal Muscle, vol. 3, No. 1, Apr. 2013, 12 pages.

(Continued)

*Primary Examiner* — Ruixiang Li
(74) *Attorney, Agent, or Firm* — Proskauer Rose LLP; Fangli Chen; Julio J. Mendez.

(57) ABSTRACT

The present invention provides, among other things, methods and compositions for treating chronic lung disorders, in particular, bronchopulmonary dysplasia (BPD). In some embodiments, a method according to the present invention includes administering to an individual who is suffering from or susceptible to BPD an effective amount of an anti-Flt-1 antibody, or antigen binding fragment thereof, such that at least one symptom or feature of BPD is reduced in intensity, severity, or frequency, or has delayed onset.

11 Claims, 22 Drawing Sheets
Specification includes a Sequence Listing.

(56) References Cited

OTHER PUBLICATIONS

Gien, J. et al., "Pathogenesis and Treatment of Bronchopulmonary Dysplasia", Curr. Opin. Pediatr., Jun. 2011, vol. 23, No. 3, pp. 304-313.

McEvoy, C. T. et al., "The Natural History of Bronchopulmonary Dysplasia (BPD): The Case for Primary Prevention", Clin. Perinatol., Dec. 2015, vol. 42, No. 4, pp. 911-931.

Messina, S. et al., "VEGF overexpression via adeno-associated virus gene transfer promotes skeletal muscle regeneration and enhances muscle function in mdx mice", The FASEB Journal, vol. 21, No. 13, Nov. 1, 2007, pp. 3737-3746.

Peisl, A. et al., "Treatment with an Anti-SFLT-1 Monoclonal Antibody Improves Lung Structure and Prevents Pulmonary Hypertension in an Experimental Model of Bronchopulmonary Dysplasia due to Preeclampsia in Infant Rats", Journal of Investigative Medicine, Database Biosis [Online], Biosciences Information Service, Philadelphia, PA, XP002759782, vol. 64, No. 1, Jan. 2016, 3 pages.

Sanz, L. et al., "Antibodies and Gene Therapy: teaching old 'magic bullets' new tricks", Trends in Immunology, vol. 25, No. 2, Feb. 1, 2004, pp. 85-91.

Sibai, B. et al., "Pre-eclampsia", Lancet, (Feb. 26, 2005), vol. 365, pp. 785-789.

Shimizu-Motohashi, Y. et al., "Angiogenesis as a novel therapeutic strategy for Duchenne muscular dystrophy through decreased ischemia and increased satellite cells", Frontiers in Physiology, vol. 5, No. 50, Jan. 27, 2014, pp. 1-17.

Tang, J.-R., et al. "Excess soluble vascular endothelial growth factor receptor-1 in amniotic fluid impairs lung growth in rates: linking preeclampsia with Bronchopulmonary dysplasia" American Journal of Physiology-Lung Cellular and Molecular Physiology, vol. 302, No. 1, Oct. 14, 2011, pp. 36-46.

Verma, M. et al., "Flt-1 haploinsufficiency ameliorates muscular dystrophy phenotype by developmentally increased vasculature in mdx mice", Human Molecular Genetics, Vo. 19, No. 21, Aug. 12, 2010, pp. 4145-4159.

Wu, Y. et al., "Anti-Vascular Endothelial Growth Factor Receptor-1 Antagonist Antibody as a Therapeutic Agent for Cancer", Clinical Cancer Research, vol. 12, No. 21, Nov. 1, 2006, pp. 6573-6584.

\* cited by examiner

SEQUENCE LISTING

```
<160> NUMBER OF SEQ ID NOS: 3

<210> SEQ ID NO 1
<211> LENGTH: 21
<212> TYPE: PRT
<213> ORGANISM: Artificial Sequence
<220> FEATURE:
<223> OTHER INFORMATION: Synthetic Oligopeptide

<400> SEQUENCE: 1

Gly Ala Pro Gly Gly Gly Gly Ala Ala Ala Ala Ala Gly Gly Gly
1               5                   10                  15

Gly Gly Gly Ala Pro
            20

<210> SEQ ID NO 2
<211> LENGTH: 39
<212> TYPE: PRT
<213> ORGANISM: Artificial Sequence
<220> FEATURE:
<223> OTHER INFORMATION: Synthetic Oligopeptide

<400> SEQUENCE: 2

Gly Ala Pro Gly Gly Gly Gly Gly Ala Ala Ala Ala Ala Gly Gly Gly
1               5                   10                  15

Gly Gly Gly Ala Pro Gly Gly Gly Gly Gly Ala Ala Ala Ala Ala Gly
```

-continued

```
                20                  25                  30
Gly Gly Gly Gly Gly Ala Pro
            35

<210> SEQ ID NO 3
<211> LENGTH: 57
<212> TYPE: PRT
<213> ORGANISM: Artificial Sequence
<220> FEATURE:
<223> OTHER INFORMATION: Synthetic Oligopeptide

<400> SEQUENCE: 3

Gly Ala Pro Gly Gly Gly Gly Ala Ala Ala Ala Ala Gly Gly Gly
1               5                   10                  15

Gly Gly Gly Ala Pro Gly Gly Gly Gly Gly Ala Ala Ala Ala Ala Gly
                20                  25                  30

Gly Gly Gly Gly Gly Ala Pro Gly Gly Gly Gly Ala Ala Ala Ala
            35                  40                  45

Ala Gly Gly Gly Gly Gly Gly Ala Pro
    50                  55
```

ANTI-FLT-1 ANTIBODIES IN TREATING BRONCHOPULMONARY DYSPLASIA

RELATED APPLICATIONS

This application is a 35 U.S.C. § 371 National Stage Application of International Application No. PCT/US16/26420, filed Apr. 7, 2016, which claims priority to U.S. Provisional Application Ser. No. 62/144,241, filed Apr. 7, 2015, the disclosure of which is hereby incorporated by reference.

INCORPORATION-BY-REFERENCE OF SEQUENCE LISTING

The content of the text file named "SHR-1188US_ST25.txt", which was created on Oct. 6, 2017 and is 2 KB in size, is hereby incorporated by reference in its entirety.

BACKGROUND

Bronchopulmonary dysplasia (BPD) is a severe, chronic lung disease that primarily affects premature infants. Premature infants can develop BPD after their lungs have been damaged from the use of supplemental oxygen and mechanical breathing aids. Infants with BPD have inflammation and scarring in the lungs and in severe cases, are at high risk for prolonged need for ventilator or oxygen support, pulmonary hypertension, recurrent respiratory infections, abnormal lung function, exercise intolerance, late neuro-developmental conditions, and even death.

Many infants with BPD recover and improve with time, however, these children are at increased risk of developing further complications, including asthma and viral pneumonia. And while most infants survive, some infants with very severe BPD will still die from the disease even after months of care.

SUMMARY OF THE INVENTION

The present invention provides, among other things, improved methods and compositions for treating chronic lung disorders, in particular, bronchopulmonary dysplasia (BPD), based on anti-Flt-1 antibody therapy. As described in the Examples below, the invention is, in part, based on the discovery that anti-Flt-1 antibodies, or antigen binding fragments thereof, can inhibit VEGF and other ligands from binding to the Flt-1 receptor, thereby increasing the amount VEGF and/or other ligands available to bind to VEGF receptors. This increased binding can induce a pro-angiogenic effect that increases capillary density and facilitates reduction of fibrosis and inflammation, and mitigation of symptoms and features associated with BPD. Indeed, as shown in the Examples, the present inventors have demonstrated that administration of an anti-Flt-1 antibody improves measures of lung pathology in BPD animal models. Therefore, the present invention provides safe and effective antibody-based therapeutics for the treatment of BPD.

In one aspect, the present invention provides methods of treating bronchopulmonary dysplasia (BPD) comprising administering to an individual in need of treatment an effective amount of an anti-Flt-1 antibody or antigen binding fragment thereof.

In some embodiments, an individual is an infant who is suffering from or susceptible to BPD. In some embodiments, an individual is pregnant with a fetus who is suffering from or susceptible to BPD.

In some embodiments, an anti-Flt-1 antibody or antigen binding fragment thereof is characterized with an ability to bind human Flt-1 at an affinity greater than $10^{-9}$M, greater than $10^{-10}$M, or greater than $10^{-12}$M in a surface plasmon resonance binding assay.

In some embodiments, an anti-Flt-1 antibody or antigen binding fragment thereof is characterized with an $IC_{50}$ below 100 pM, below 10 pM, or below 1 pM in a competition assay with human Flt-1.

In some embodiments, a competition assay is inhibition of binding of VEGF to human Flt-1. In some embodiments, a competition assay is inhibition of binding of PLGF to human Flt-1.

In some embodiments, an anti-Flt-1 antibody or antigen binding fragment thereof does not bind to VEGFR2 and/or VEGFR3.

In some embodiments, an anti-Flt-1 antibody or antigen binding fragment thereof does not bind to a mouse or monkey Flt-1.

In some embodiments, an anti-Flt-1 antibody or antigen binding fragment thereof binds to a mouse and/or monkey Flt-1.

In some embodiments, an anti-Flt-1 antibody or antigen binding fragment thereof is selected from the group consisting of IgG, F(ab')$_2$, F(ab)$_2$, Fab', Fab, ScFvs, diabodies, triabodies and tetrabodies. In some embodiments, an anti-Flt-1 antibody or antigen binding fragment thereof is IgG. In some embodiments, an anti-Flt-1 antibody or antigen binding fragment thereof is IgG1.

In some embodiments, an anti-Flt-1 antibody or antigen binding fragment thereof is a monoclonal antibody. In some embodiments, a monoclonal antibody is a humanized monoclonal antibody. In some embodiments, a humanized monoclonal antibody contains a human Fc region. In some embodiments, a Fc region contains one or more mutations that enhance the binding affinity between the Fc region and the FcRn receptor such that the in vivo half-life of the antibody is prolonged. In some embodiments, a Fc region contains one or more mutations at one or more positions corresponding to Thr 250, Met 252, Ser 254, Thr 256, Thr 307, Glu 380, Met 428, His 433, and/or Asn 434 of human IgG1.

In some embodiments, an anti-Flt-1 antibody or antigen binding fragment thereof is administered parenterally. In some embodiments, parenteral administration is selected from intravenous, intradermal, intrathecal, inhalation, transdermal (topical), intraocular, intramuscular, subcutaneous, pulmonary delivery, and/or transmucosal administration. In some embodiments, parenteral administration is intravenous administration.

In some embodiments, an anti-Flt-1 antibody or antigen binding fragment thereof is administered orally.

In some embodiments, an anti-Flt-1 antibody or antigen binding fragment thereof is administered bimonthly, monthly, triweekly, biweekly, weekly, daily, or at variable intervals.

In some embodiments, an anti-Flt-1 antibody or antigen binding fragment thereof is delivered to one or more target tissues selected from lungs and heart. In some embodiments, an anti-Flt-1 antibody or antigen binding fragment thereof is delivered to the lungs. In some embodiments, an anti-Flt-1 antibody, or an antigen binding fragment thereof, is delivered to the heart.

In some embodiments, administration of an anti-Flt-1 antibody or antigen binding fragment thereof results in growth of healthy lung tissue, decreased lung inflammation, increased alveologenesis, increased angiogenesis, improved structure of pulmonary vascular bed, reduced lung scarring, improved lung growth, reduced respiratory insufficiency, improved exercise tolerance, reduced adverse neurological outcome, and/or improved pulmonary function relative to a control.

In some embodiments, the present invention provides a method further comprising co-administering at least one additional agent or therapy selected from a surfactant, oxygen therapy, ventilator therapy, a steroid, vitamin A, inhaled nitric oxide, high calorie nutritional formulation, a diuretic, and/or a bronchodilator.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DEFINITIONS

Figure 1:
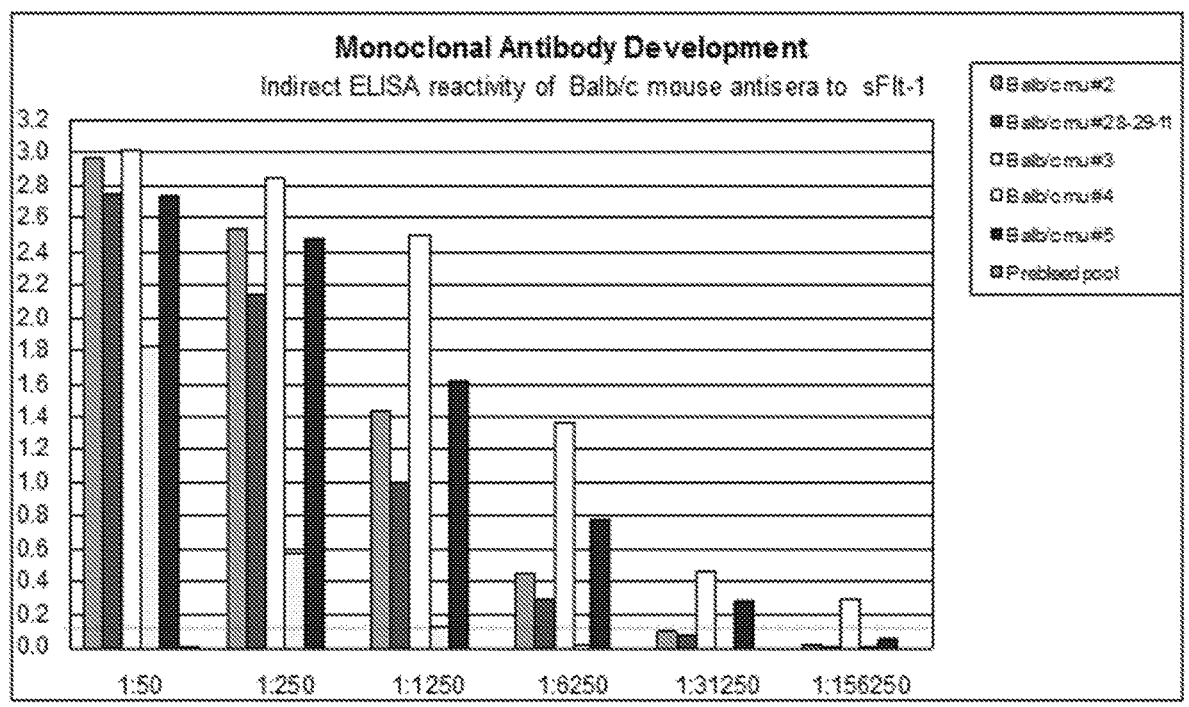
FIG. 1 shows exemplary results illustrating the anti-soluble human Flt-1 antiserum titer of mice immunized with soluble human Flt-1 antigen.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin-binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. In certain embodiments, an antibody may be a member of the IgG immunoglobulin class. As used herein, the terms "antibody fragment" or "characteristic portion of an antibody" are used interchangeably and refer to any derivative of an antibody that is less than full-length. In general, an antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multimolecular complex. A functional antibody fragment typically comprises at least about 50 amino acids and more typically comprises at least about 200 amino acids. In some embodiments, an antibody may be a human antibody. In some embodiments, an antibody may be a humanized antibody.

Antigen binding fragment: As used herein, the term "antigen binding fragment" refers to a portion of an immunoglobulin molecule that contacts and binds to an antigen (i.e., Flt-1).

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the binding of one or more VEGF ligands, is considered to be biologically active.

Carrier or diluent: As used herein, the terms "carrier" and "diluent" refer to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties that are similar to that of the substituted amino acid. Desirable similar chemico-physical properties include similarities in charge, bulkiness, hydrophobicity, hydrophilicity, and the like.

Fusion protein: As used herein, the term "fusion protein" or "chimeric protein" refers to a protein created through the joining of two or more originally separate proteins, or portions thereof. In some embodiments, a linker or spacer will be present between each protein.

Half-life: As used herein, the term "half-life" is the time required for a quantity such as protein concentration or activity to fall to half of its value as measured at the beginning of a time period.

Hypertrophy: As used herein the term "hypertrophy" refers to the increase in volume of an organ or tissue due to the enlargement of its component cells.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subjects) in the absence of the treatment described herein. A "control subject" is a subject afflicted with the same form of disease as the subject being treated, who is about the same age as the subject being treated.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

Pharmaceutically acceptable: As used herein, the term "pharmaceutically acceptable" refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, the term "polypeptide" refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: As used herein, the term "protein" refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., BPD). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., BPD). In some embodiments a reference sample or group of reference samples are from individuals comparable to a particular individual. In some embodiments, relative risk is 0, 1, 2, 3, 4, 5, 6, 7, 8, 9, 10, or more.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: As used herein, the phrase "substantial homology refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: As used herein, the phrase "substantial identity" is used to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, BPD) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target tissues: As used herein, the term "target tissues" refers to any tissue that is affected by a disease to be treated such as BPD. In some embodiments, target tissues include those tissues that display disease-associated pathology, symptom, or feature, including but not limited to lung inflammation, lung scarring, impaired lung growth, early lung injury, prolonged respiratory insufficiency, lung infections, exercise intolerance, and adverse neurological outcome.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating chronic lung disorders, in particular, bronchopulmonary dysplasia (BPD), based on the use of anti-Flt-1 antibodies, or antigen binding fragments thereof, as therapeutics for treating BPD. In some embodiments, the present invention provides methods of treating BPD including administering to an individual who is suffering from or susceptible to BPD an effective amount of an Flt-1 antibody or antigen binding fragment thereof such that at least one symptom or feature of BPD is reduced in intensity, severity, or frequency, or has delayed onset.

Various aspects of the invention are described in detail in the following sections. The use of sections is not meant to limit the invention. Each section can apply to any aspect of the invention. In this application, the use of "or" means "and/or" unless stated otherwise.

Bronchopulmonary Dysplasia (BPD)

With the introduction of surfactant therapy, maternal steroids, new ventilator strategies, aggressive management of the patent ductus arteriosus, improved nutrition, and other treatments, the clinical course and outcomes of premature newborns with RDS have dramatically changed over the past 30 years. It has recently been demonstrated that about two thirds of infants who develop BPD have only mild respiratory distress at birth. This suggests that developmental timing of lung injury is a critical factor in the etiology of BPD.

In parallel with this changing epidemiologic and clinical pattern, key features of lung histology in BPD have also changed. There is now growing recognition that infants with persistent lung disease after premature birth have a different clinical course and pathology than was traditionally observed in infants dying with BPD during this presurfactant era. The classic progressive stages that first characterized BPD are often absent owing to changes in clinical management, and BPD has clearly changed from being predominantly defined by the severity of acute lung injury to its current characterization, which is primarily defined by a disruption of distal lung growth. Thus, the so-called new BPD of the postsurfactant period represents inhibition of lung development with altered lung structure, growth, and function of the distal airspaces and vasculature. Physiologically, this suggests a marked reduction in alveolo-capillary surface area, potentially contributing to impaired gas exchange with increased risk for exercise intolerance, pulmonary hypertension, and poor tolerance of acute respiratory infections.

Pathogenesis of BPD

BPD represents the response of the lung to injury during a critical period of lung growth, that is, during the canalicular period (17 to 26 weeks in the human), a time during which airspace septation and vascular development increase dramatically. In some embodiments, factors that increase the susceptibility of the premature newborn to the development of BPD, include surfactant deficiency, decreased antioxidant defenses, impaired epithelial ion and water transport function, and lung structural immaturity. In some embodiments, lung injury after premature birth and the subsequent arrest of lung growth results from complex interactions between multiple adverse stimuli, including inflammation, hyperoxia, mechanical ventilation, and infection, of the poorly defended developing lung. In some embodiments, prenatal exposure to proinflammatory cytokines, such as TNF-α, IL-6, IL-8, and others, due to maternal chorioamnionitis, enhance lung maturation in utero, but increase the risk for BPD.

Hyperoxia and oxidant stress are critical factors in the development of BPD. In some embodiments, the transition of the premature newborn from the low-oxygen tension environment of the normal fetus to the relative hyperoxia of extrauterine life increases the risk for BPD with decreased alveolarization and a dysmorphic vasculature. In some embodiments, the premature change in the oxygen environment impedes normal epithelial-mesenchymal interactions and leads to alterations in endothelial cell survival, differentiation, and organization in the microvasculature. In some embodiments, a premature infant is especially susceptible to reactive oxidant species (ROS)-induced damage owing to the lack of adequate antioxidants after premature birth. In some embodiments, antioxidant enzymes [e.g., superoxide dismutase (SOD), catalase, and glutathione peroxidase] markedly increase during late gestation. In some additional embodiments, the ability to increase synthesis of antioxidant enzymes in response to hyperoxia is decreased in preterm animals, so premature birth may precede the normal up-regulation of antioxidants, which persists during early postnatal life. In some embodiments, endothelial and alveolar type II cells are extremely susceptible to hyperoxia and ROS-induced injury, leading to increased edema, cellular dysfunction, and impaired cell survival and growth.

In some embodiments, even in the absence of overt signs of baro- or volutrauma, treatment of premature neonates with mechanical ventilation initiates and promotes lung injury with inflammation and permeability edema, and contributes to BPD. In some embodiments, ventilator-associated lung injury (VALI) results from stretching distal airway epithelium and capillary endothelium, which increases permeability edema, inhibits surfactant function, and provokes a complex inflammatory cascade. In some embodiments, even brief periods of positive-pressure ventilation, such as during resuscitation in the delivery room, can cause bronchiolar epithelial and endothelial damage in the lung, setting the stage for progressive lung inflammation and injury.

Lung inflammation, whether induced prior to birth (from chorioamnionitis) or during the early postnatal period (due to hyperoxia or VALI) plays a prominent role in the development of BPD. In some embodiments, the risk for BPD is associated with sustained increases in tracheal fluid neutrophil counts, activated macrophages, high concentrations of lipid products, oxidant-inactivated α-1-antitrypsin activity, and proinflammatory cytokines, including IL-6 and IL-8, and decreased IL-10 levels. In some embodiments, release of early response cytokines, such as TNF-α, IL-1β, IL-8, and TGF-β, by macrophages and the presence of soluble adhesion molecules (i.e., selectins) may impact other cells to release chemoattractants that recruit neutrophils and amplify the inflammatory response. In some embodiments, elevated concentrations of proinflammatory cytokines in conjunction with reduced anti-inflammatory products (i.e., IL-10) appear in tracheal aspirates within a few hours of life in infants subsequently developing BPD. In some embodiments, increased elastase and collagenase release from activated neutrophils may directly destroy the elastin and collagen framework of the lung, and markers of collagen and elastin degradation can be recovered in the urine of infants with BPD. In some embodiments, infection from relatively low virulence organisms, such as airway colonization with *Ureaplasma urealyticum*, may augment the inflammatory response, further increasing to the risk for BPD. In some embodiments, other factors, such as nutritional deficits and genetic factors, such as vitamin A and E deficiency or single nucleotide polymorphism variants of the surfactant proteins, respectively, are likely to increase risk for BPD in some premature newborns.

Pulmonary Circulation in BPD

In addition to adverse effects on the airway and distal airspace, acute lung injury also impairs growth, structure, and function of the developing pulmonary circulation after premature birth. In some embodiments, endothelial cells are particularly susceptible to oxidant injury through hyperoxia or inflammation. In some embodiments, the media of small pulmonary arteries undergoes striking changes, including smooth muscle cell proliferation, precocious maturation of immature mesenchymal cells into mature smooth muscle cells, and incorporation of fibroblasts/myofibroblasts into the vessel wall. In some embodiments, structural changes in the lung vasculature contribute to high pulmonary vascular resistance (PVR) through narrowing of the vessel diameter and decreased vascular compliance. In some embodiments, in addition to these structural changes, the pulmonary circulation is further characterized by abnormal vasoreactivity, which also increases PVR. In some embodiments, decreased angiogenesis may limit vascular surface area, causing further elevations of PVR, especially in response to high cardiac output with exercise or stress.

Overall, early injury to the lung circulation leads to the rapid development of pulmonary hypertension, which contributes significantly to the morbidity and mortality of severe BPD. In some embodiments, high mortality rates occur in infants with BPD and pulmonary hypertension who require prolonged ventilator support. In some embodiments, pulmonary hypertension is a marker of more advanced BPD, and elevated PVR also causes poor right ventricular function, impaired cardiac output, limited oxygen delivery, increased pulmonary edema and, perhaps, a higher risk for sudden death. In some embodiments, physiologic abnormalities of the pulmonary circulation in BPD include elevated PVR and abnormal vasoreactivity, as evidenced by the marked vasoconstrictor response to acute hypoxia. In some embodiments, even mild hypoxia causes marked elevations in pulmonary artery pressure in infants with modest basal levels of pulmonary hypertension. In some embodiments, treatment levels of oxygen saturations above 92-94% effectively lower pulmonary artery pressure. In some embodiments, strategies to lower pulmonary artery pressure or limit injury to the pulmonary vasculature may limit the subsequent development of pulmonary hypertension in BPD.

Finally, pulmonary hypertension and right heart function remain major clinical concerns in infants with BPD. In some embodiments, pulmonary vascular disease in BPD also includes reduced pulmonary artery density owing to impaired growth, which contributes to physiologic abnormalities of impaired gas exchange, as well as to the actual pathogenesis of BPD. In some embodiments, impaired angiogenesis impedes alveolarization and strategies that preserve and enhance endothelial cell survival, growth, and function provide therapeutic approaches for the prevention of BPD.

Altered Signaling of Angiogenic Factors in BPD

Multiple growth factors and signaling systems play important roles in normal lung vascular growth. In some embodiments, premature delivery and changes in oxygen tension, inflammatory cytokines, and other signals alter normal growth factor expression and signaling and thus lung/lung vascular development. In some embodiments, the growth factor is VEGF. Impaired VEGF signaling has been associated with the pathogenesis of BPD in the clinical setting. In some embodiments, VEGF is found to be lower in tracheal fluid samples from premature neonates who subsequently develop BPD than those who do not develop chronic lung disease (185). In some embodiments, hyperoxia down-regulates lung VEGF expression, and pharmacologic inhibition of VEGF signaling impairs lung vascular growth and inhibits alveolarization. The biologic basis for impaired VEGF signaling leading to decreased vascular growth and impaired alveolarization is well established.

Vascular Growth and Alveolarization

As described above, close coordination of growth between airways and vessels is essential for normal lung development. In some embodiments, failure of pulmonary vascular growth during a critical period of lung growth (saccular or alveolar stages of development) decreases septation and ultimately contributes to the lung hypoplasia that characterizes BPD. In some embodiments, angiogenesis is involved in alveolarization during lung development and mechanisms that injure and inhibit lung vascular growth may impede alveolar growth after premature birth. In some embodiments, inhibition of lung vascular growth during a critical period of postnatal lung growth impairs alveolarization.

Flt-1 Receptor

Flt-1 receptor, also known as vascular endothelial growth factor receptor 1, is a receptor that is encoded by the FLT1 gene. The vascular endothelial growth factor (VEGF) family of signal glycoproteins act as potent promoters of angiogenesis during embryogenesis and postnatal growth. Specifically, the binding of the VEGF-A ligand with the VEGF receptors has been shown to promote vascular permeability and also trigger endothelial cell migration, proliferation, and survival, and the newly formed endothelial cells provide the basic structure of new vasculatures. The dominant VEGF signal molecule for angiogenesis, VEGF-A, mediates its signal through VEGF receptor-1 (VEGFR-1, also known as Flt-1) and VEGF receptor-2 (VEGFR-2, also known as Flk-1). A soluble form of Flt-1 (sFlt-1) also exists, but lacks an intracellular signaling domain and thus is believed to only serve in a regulatory capacity by sequestering VEGF-A or other ligands that bind to it. sFlt-1 and other molecules containing Flt-1 binding sites that are not linked to an intracellular signal transduction pathway are referred to as "decoy receptors". Flt-1 and Flk-1 receptors contain an extracellular VEGF-A-binding domain and an intracellular tyrosine kinase domain, and both show expression during the developmental stage and tissue regeneration in hemangioblasts and endothelial cell lineages. Flt-1 has about 10 times greater binding affinity for VEGF-A (Kd ~2-10 pM) compared to Flk-1, but the weaker tyrosine kinase domain indicates that angiogenic signal transduction following VEGF-A binding to Flt-1 is comparably weaker than the Flk-1 signal. As such, homozygous Flt-1 gene knockout mice die in the embryonic stage from endothelial cell overproduction and blood vessel disorganization. Inversely, homozygous Flk-1 gene knockout mice die from defects in the development of organized blood vessels due to lack of yolk-sac blood island formation during embryogenesis. Both the Flt-1 and Flk-1 receptors are needed for normal development, but selective augmentation in VEGF-A concentration may allow for greater binding to the Flk-1 receptor and induce a pro-angiogenic effect that increases capillary density and facilitates reduction of fibrosis and inflammation, and mitigation of symptoms and features associated with BPD.

As used herein, the term "Flt-1 receptor" refers to both soluble and membrane associated Flt-1 receptors, or functional fragments thereof.

Anti-Flt-1 Antibodies

As used herein, the term "anti-Flt-1 antibodies" refers to any antibodies, or antigen binding fragments thereof, that bind to an Flt-1 receptor (e.g., soluble or membrane associated Flt-1 receptor). In some embodiments, anti-Flt-1 antibodies are produced that bind with high affinity to Flt-1 receptors. Without wishing to be bound by theory, it is believed that anti-Flt-1 antibody binding to Flt-1 receptors inhibits one or more endogenous ligands from binding to Flt-1 and thereby allowing a greater amount of available ligand to associate with other VEGF receptors, such as the Flk-1 receptor. Increased activation of the Flk-1 receptor could increases capillary density and facilitates reduction of fibrosis and inflammation, and mitigation of symptoms and features associated with BPD. In some embodiments, antibody binding to Flt-1 receptors increases the amount of VEGF available to bind to other VEGF receptors. In some embodiments, antibody binding to Flt-1 receptors increases the amount of placental growth factor (PLGF) available to bind to other VEGF receptors.

In some embodiments, an anti-Flt-1 antibody, or an antigen binding fragment thereof, binds human Flt-1 with an affinity greater than about $10^{-9}$M, greater than about $10^{-10}$ M, greater than about $0.5 \times 10^{-10}$ M greater than about $10^{-11}$M, greater than about $0.5 \times 10^{-11}$M, greater than about $10^{-12}$M, or greater than about $0.5 \times 10^{-12}$M. The affinity of an Flt-1 antibody may be measured, for example, in a surface plasmon resonance assay, such as a BIACORE assay.

In some embodiments, an anti-Flt-1 antibody, or an antigen binding fragment thereof, is characterized by an $IC_{50}$ below 100 pM, below 10 pM, or below 1 pM in a competition assay with human Flt-1.

In some embodiments, an anti-Flt-1 antibody, or an antigen binding fragment thereof inhibits the binding and/or activity of VEGF at the Flt-1 receptor. In some embodiments, an anti-Flt-1 antibody, or an antigen binding fragment thereof, is characterized by an $IC_{50}$ below 100 pM, below 10 pM, or below 1 pM for inhibition of binding of VEGF to human Flt-1 in a competition assay.

In some embodiments, an anti-Flt-1 antibody, or an antigen binding fragment thereof inhibits the binding and/or activity of PLGF at the Flt-1 receptor. In some embodiments, an anti-Flt-1 antibody, or an antigen binding fragment thereof, is characterized by an $IC_{50}$ below 100 pM, below 10 pM, or below 1 pM for inhibition of binding of PLGF to human Flt-1 in a competition assay.

In some embodiments, an anti-Flt-1 antibody, or an antigen binding fragment thereof selectively binds Flt-1 and has minimal or no appreciable binding to other VEGF receptors. In some embodiments, an anti-Flt-1 antibody, or an antigen binding fragment thereof selectively binds Flt-1 and has minimal or no appreciable binding to VEGFR2 (Flk-1) and/or VEGFR3 (Flt-4).

In some embodiments, an anti-Flt-1 antibody, or an antigen binding fragment thereof selectively binds human Flt-1, and has minimal or no appreciable binding to other mammalian Flt-1 receptors (e.g., with a binding affinity less than $10^{-7}$M or $10^{-6}$M). In some embodiments, an anti-Flt-1 antibody, or an antigen binding fragment thereof selectively binds human Flt-1 and does not bind to monkey Flt-1. In some embodiments, an anti-Flt-1 antibody, or an antigen binding fragment thereof selectively binds human Flt-1 and does not bind to mouse Flt-1.

In some embodiments, an anti-Flt-1 antibody, or an antigen binding fragment thereof binds human Flt-1 as well as monkey Flt-1. In some embodiments an anti-Flt-1 antibody, or an antigen binding fragment thereof binds human Flt-1 as well as mouse Flt-1.

In some embodiments, an anti-Flt-1 antibody, or an antigen binding fragment thereof, is selected from the group consisting of IgG, F(ab')$_2$, F(ab)$_2$, Fab', Fab, ScFvs, diabodies, triabodies and tetrabodies.

In some embodiments an anti-Flt-1 antibody, or an antigen binding fragment thereof, is IgG. In some embodiments an anti-Flt-1 antibody, or an antigen binding fragment thereof, is IgG1.

In some embodiments, a suitable anti-Flt-1 antibody contains an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. Particularly suitable Fc domains include those derived from human or humanized antibodies.

It is contemplated that improved binding between Fc domain and the FcRn receptor results in prolonged serum half-life. Thus, in some embodiments, a suitable Fc domain comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Thr 250, Met 252, Ser 254, Thr 256, Thr 307, Glu 380, Met 428, His 433, and/or Asn 434 of human IgG1.

In some embodiments, an anti-FLT-1 antibody or antigen binding fragment contains a spacer and/or is linked to another entity. In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAP (SEQ ID NO: 1) (GAG linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAAGGGGGGAP (SEQ ID NO: 2) (GAG2 linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAAGGGGG GAPGGGGGAAAAAGGGGG GAP (SEQ ID NO: 3) (GAG3 linker).

Production of Anti-Flt-1 Antibodies and Antigen Binding Fragments

A recombinant anti-Flt-1 antibody or antigen binding fragment suitable for the present invention may be produced by any available means. For example, a recombinant anti-Flt-1 antibody or antigen binding fragment may be recombinantly produced by utilizing a host cell system engineered to express a recombinant anti-Flt-1 antibody or antigen binding fragment-encoding nucleic acid.

Where antibodies are recombinantly produced, any expression system can be used. To give but a few examples, known expression systems include, for example, egg, baculovirus, plant, yeast, or mammalian cells.

In some embodiments, recombinant anti-Flt-1 antibody or antigen binding fragments suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); and monkey kidney CV1 line transformed by SV40 (COS-7, ATCC CRL 1651).

In some embodiments, the present invention provides recombinant anti-Flt-1 antibody or antigen binding fragment produced from human cells. In some embodiments, the present invention provides anti-Flt-1 antibody or antigen binding fragment produced from CHO cells.

Pharmaceutical Composition and Administration

The present invention further provides a pharmaceutical composition containing an anti-Flt-1 antibody or antigen binding fragment described herein and a physiologically acceptable carrier or excipient.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Routes of Administration

An anti-Flt-1 antibody or antigen binding fragment described herein (or a composition or medicament containing an anti-Flt-1 antibody or antigen binding fragment described herein) is administered by any appropriate route. In some embodiments, an anti-Flt-1 antibody or antigen binding fragment protein or a pharmaceutical composition containing the same is administered parenterally. Parenteral administration may be intravenous, intradermal, intrathecal, inhalation, transdermal (topical), intraocular, intramuscular, subcutaneous, intramuscular, and/or transmucosal administration. In some embodiments, an anti-Flt-1 antibody or antigen binding fragment or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, an anti-Flt-1 antibody or antigen binding fragment thereof or a pharmaceutical composition containing the same is administered intravenously. In some embodiments, an anti-Flt-1 antibody or antigen binding fragment thereof or a pharmaceutical composition containing the same is administered intra-arterially. In some embodiments, an anti-Flt-1 antibody or antigen binding fragment or a pharmaceutical composition containing the same is administered orally. More than one route can be used concurrently, if desired.

In some embodiments, administration results only in a localized effect in an individual, while in other embodiments, administration results in effects throughout multiple portions of an individual, for example, systemic effects. Typically, administration results in delivery of an anti-Flt-1 antibody or antigen binding fragment to one or more target tissues including but not limited lungs and heart.

Dosage Forms and Dosing Regimen

In some embodiments, a composition is administered in a therapeutically effective amount and/or according to a dosing regimen that is correlated with a particular desired outcome (e.g., with treating or reducing risk for a chronic lung disorder, such as bronchopulmonary dysplasia).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an anti-Flt-1 antibody or antigen binding fragment thereof is administered at a therapeutically effective amount. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a chronic lung disorder, such as bronchopulmonary dysplasia.

In some embodiments, a formulation comprising an anti-Flt-1 antibody or antigen binding fragment described herein administered as a single dose. In some embodiments, a formulation comprising an anti-Flt-1 antibody or antigen binding fragment described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an anti-Flt-1 antibody or antigen binding fragment described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an anti-Flt-1 antibody or antigen binding fragment described herein is administered at regular intervals indefinitely. In some embodiments, a formulation comprising an anti-Flt-1 antibody or antigen binding fragment described herein is administered at regular intervals for a defined period.

In some embodiments, a formulation comprising an anti-Flt-1 antibody or antigen binding fragment described herein is administered prenatally. In some embodiments, a formulation comprising an anti-Flt-1 antibody or antigen binding fragment described herein is administered postnatally.

In some embodiments, a formulation comprising an anti-Flt-1 antibody or antigen binding fragment described herein is administered at a dose of about 0.5 mg/kg body weight, about 1.0 mg/kg body weight, about 10 mg/kg body weight or about 20 mg/kg body weight.

In some embodiments, a formulation comprising an anti-Flt-1 antibody or antigen binding fragment described herein is administered at a dose ranging from about 0.5 mg/kg body weight to about 20 mg/kg body weight, for example about 1 mg/kg body weight to about 10 mg/kg body weight.

In some embodiments, a formulation comprising an anti-Flt-1 antibody or antigen binding fragment described herein is administered to an adult at a unit dose of about 35 mg, about 70 mg, about 700 mg or about 1400 mg. In some embodiments, a formulation comprising an anti-Flt-1 antibody or antigen binding fragment described herein is administered at a dose ranging from about 35 mg to about 1400 mg, for example about 70 mg to about 700 mg.

In some embodiments, a formulation comprising an anti-Flt-1 antibody or antigen binding fragment described herein is administered to an infant at a unit dose of about 2 mg, about 4 mg, about 40 mg or about 80 mg. In some embodiments, a formulation comprising an anti-Flt-1 antibody or antigen binding fragment described herein is administered at a dose ranging from about 2 mg to about 80 mg, for example about 4 mg to about 40 mg.

In some embodiments, administration of an anti-Flt-1 antibody, or an antigen binding fragment thereof reduces the intensity, severity, or frequency, or delays the onset of at least one BPD sign or symptom. In some embodiments administration of an anti-Flt-1 antibody, or an antigen binding fragment thereof reduces the intensity, severity, or frequency, or delays the onset of at least one BPD sign or symptom selected from the group consisting of lung inflammation, lung scarring, impaired lung growth, early lung injury, prolonged respiratory insufficiency, lung infections, exercise intolerance, and adverse neurological outcome.

Combination Therapy

In some embodiments, an anti-Flt-1 antibody or antigen binding fragment is administered in combination with one or more known therapeutic agents (e.g., corticosteroids) currently used for treatment of a muscular dystrophy. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

EXAMPLES

Example 1. Generation and Characterization of High Affinity Anti-Flt-1 Antibodies Antibody 01A04

Figure 2:
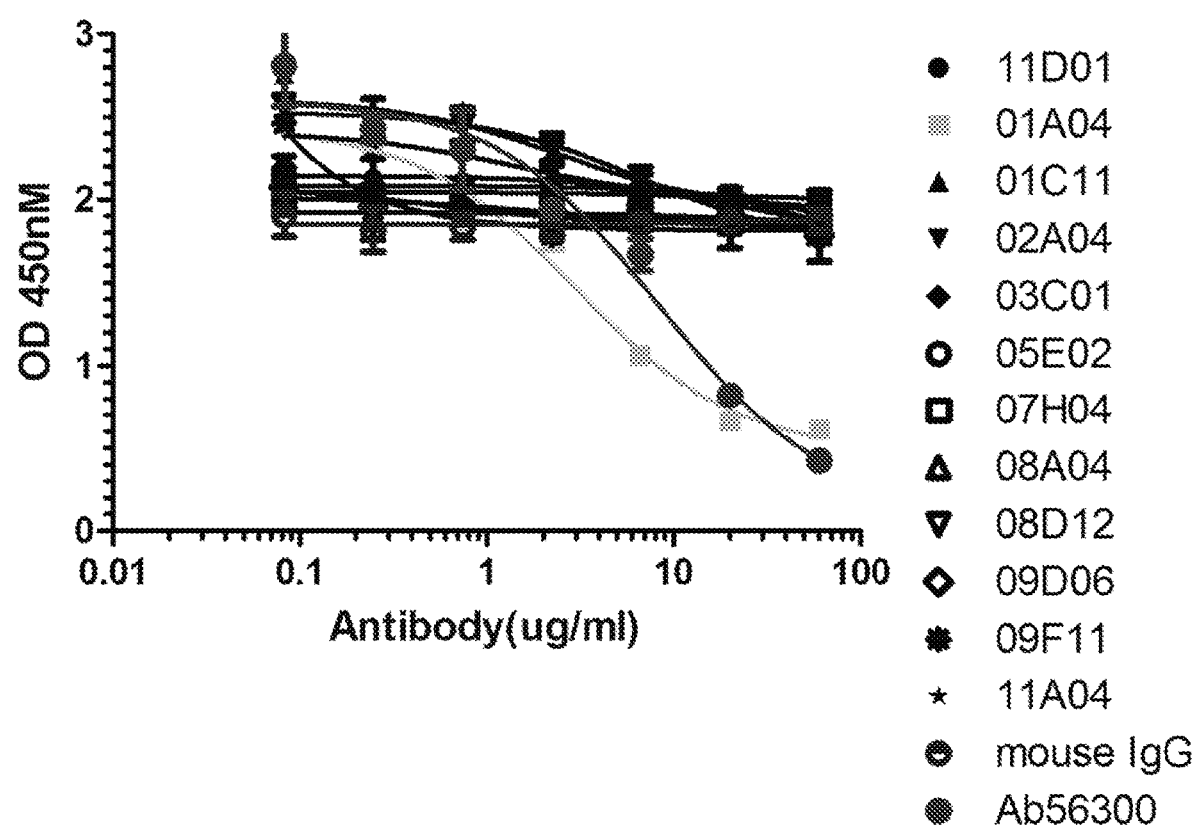
FIG. 2 shows exemplary results illustrating competitive binding of monoclonal antibodies with human soluble Flt-1 in an ELISA.

An antibody was generated against soluble Flt-1 using traditional mouse monoclonal antibody methodology. Briefly, Balb/c mice were immunized with recombinant human soluble Flt-1 (purchased from ABCAM). On day 20 post-immunization, animals were titered for anti-sFlt-1 production by ELISA (FIG. 1). One mouse was found to be a high titer responder; this animal was subsequently boosted with antigen and sacrificed 5 days later. Spleen and lymph node cells from this animal were fused to mouse myeloma partners to produce hybridomas. Hybridoma supernatants were screened versus sFlt-1 antigen, and positive responders were scaled up and re-assayed for binding to both human and mouse sFlt-1, as well as the ability to compete with sFlt-1 for VEGF binding. There were no cross reactive hybridomas that could bind to both human and mouse sFlt-1. However, among human sFlt-1 reactive hybridomas, several sFlt-1:VEGF antagonists were identified by competition ELISA (see FIG. 2 for a representative experiment). The most potent of these, fusion partner 01A04, was subjected to three rounds of single cell cloning to achieve monoclonal antibody 01A04. This antibody was further characterized for binding affinity to sFlt-1 antigen (ELISA, BIACORE and FACs); IC50 in sFlt-1:VEGF competition ELISA; and performance in cell based assays.

Antibody 01A04 Characterization—Binding

Figure 3:
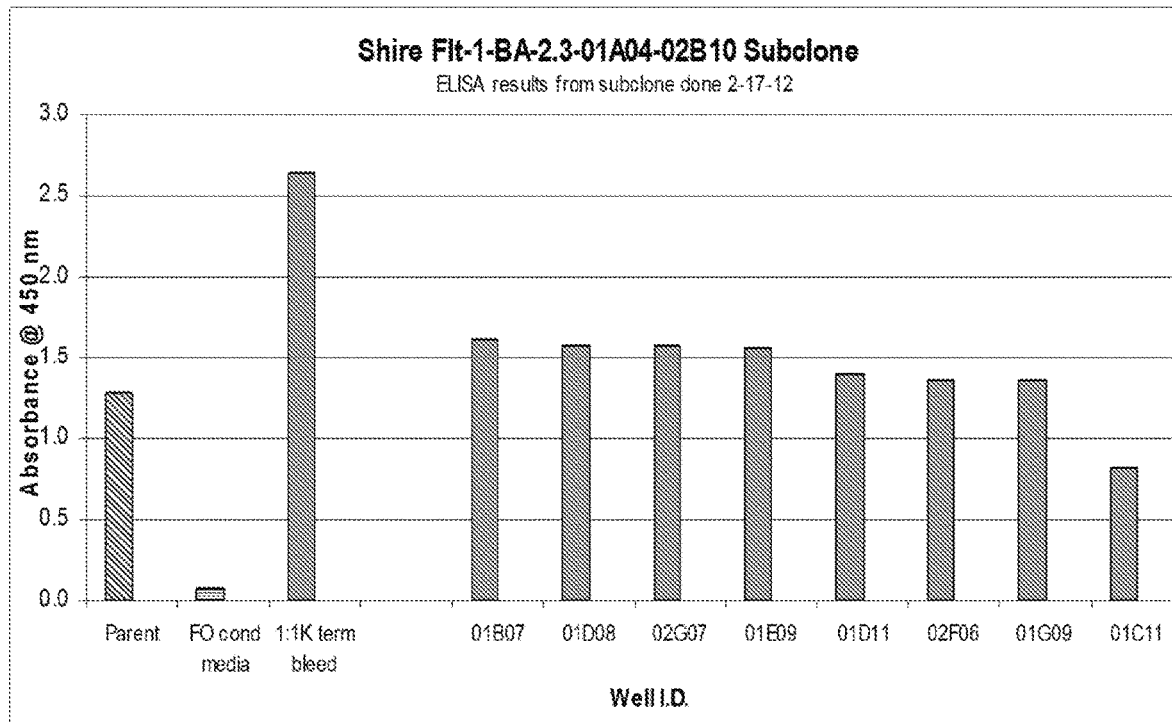
FIG. 3 shows exemplary monoclonal antibody binding to soluble human Flt-1.
Figure 4:
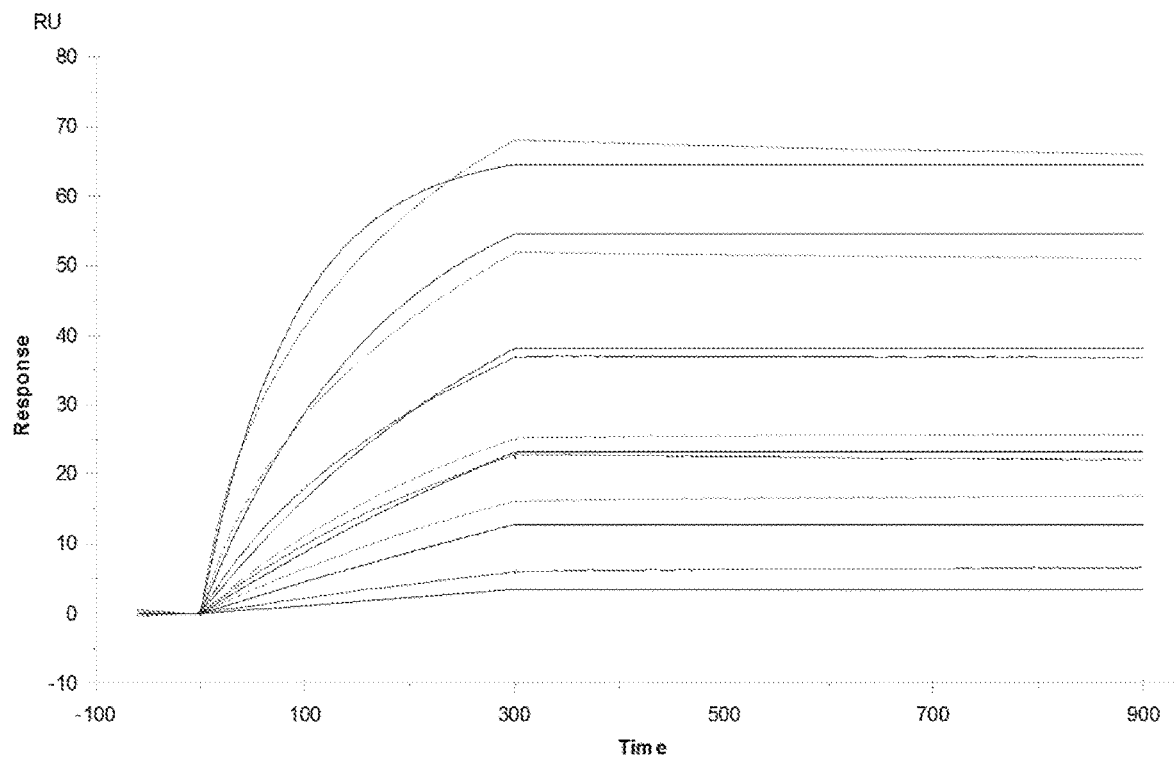
FIG. 4 shows exemplary results illustrating monoclonal antibody binding to soluble human Flt-1 via surface plasmon resonance (BIACORE) assay.

Following cloning and sub-cloning of the fusion partner parent, multiple sub-clones of the 01A04 parent demonstrated binding to immobilized soluble Flt-1 (FIG. 3). One of these subclones, monoclonal 01A04-02B10-02G07 was chosen for scale up and cell banking based upon antigen binding, clone morphology and viability. The binding constant of 01A04-02B10-02G07 for sFlt-1 antigen was determined via surface plasmon resonance methodology (BIACORE, see FIG. 4). Monoclonal antibody 01A04-02B10-02G07 is a sub-nanomolar binder to human sFlt-1.

Antibody 01A04 Characterization—Cross-Reactivity

Figure 5:
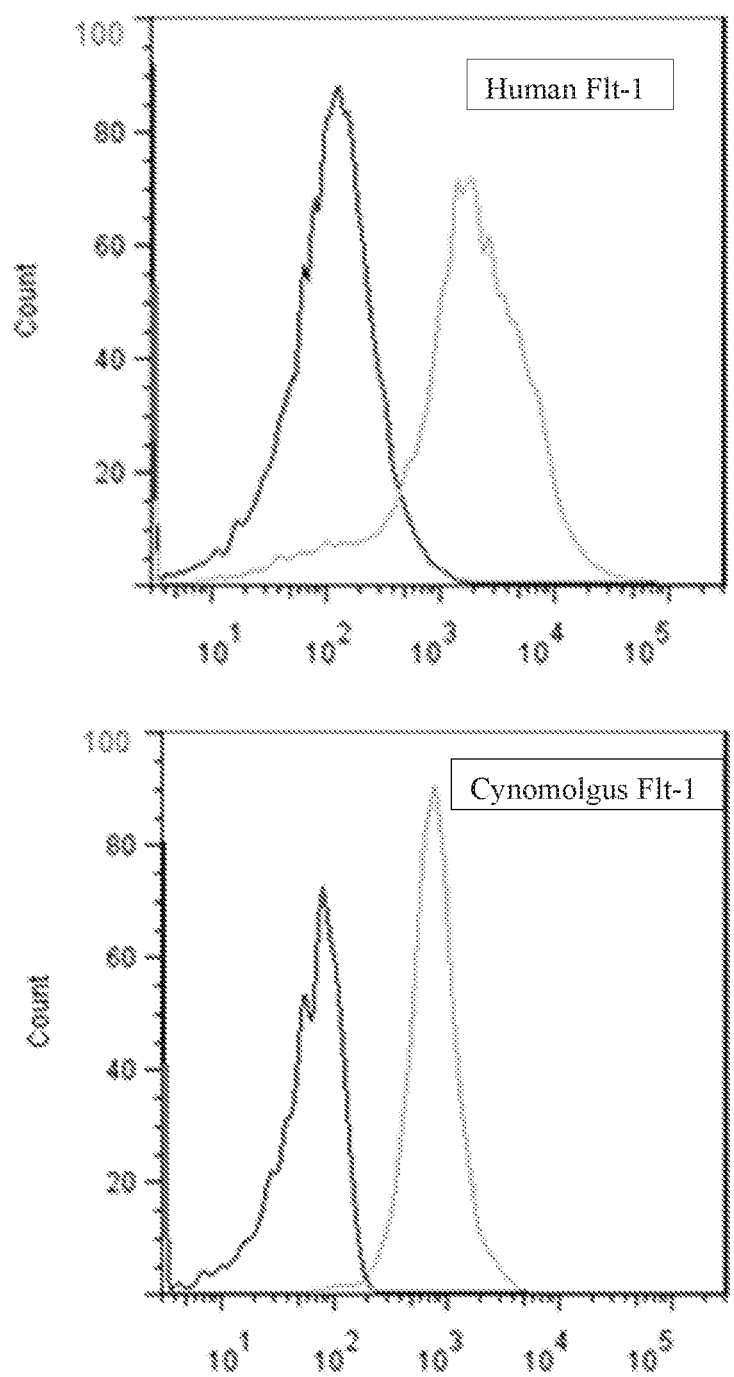
FIG. 5 shows exemplary results illustrating cross-reactivity of monoclonal antibody binding with cyno (monkey) Flt-1.

Binding of monoclonal antibody 01A04 to the Flt-1 receptor expressed on cells was tested with FACS. Three transfected cell lines were tested expressing human, mouse or cyno Flt-1. Binding to all three cell lines was tested by incubating the cells with antibody for one hour. Binding of the antibody to the cells was then revealed with an anti-mouse IgG PE antibody. Results are shown in FIG. 5. Consistent with ELISA and BIACORE data, monoclonal antibody 01A04 does not bind to mouse Flt-1. However, the antibody does bind to human and cynomolgus Flt-1 expressed on cells.

Antibody 01A04 Characterization—Competition

Figure 6:
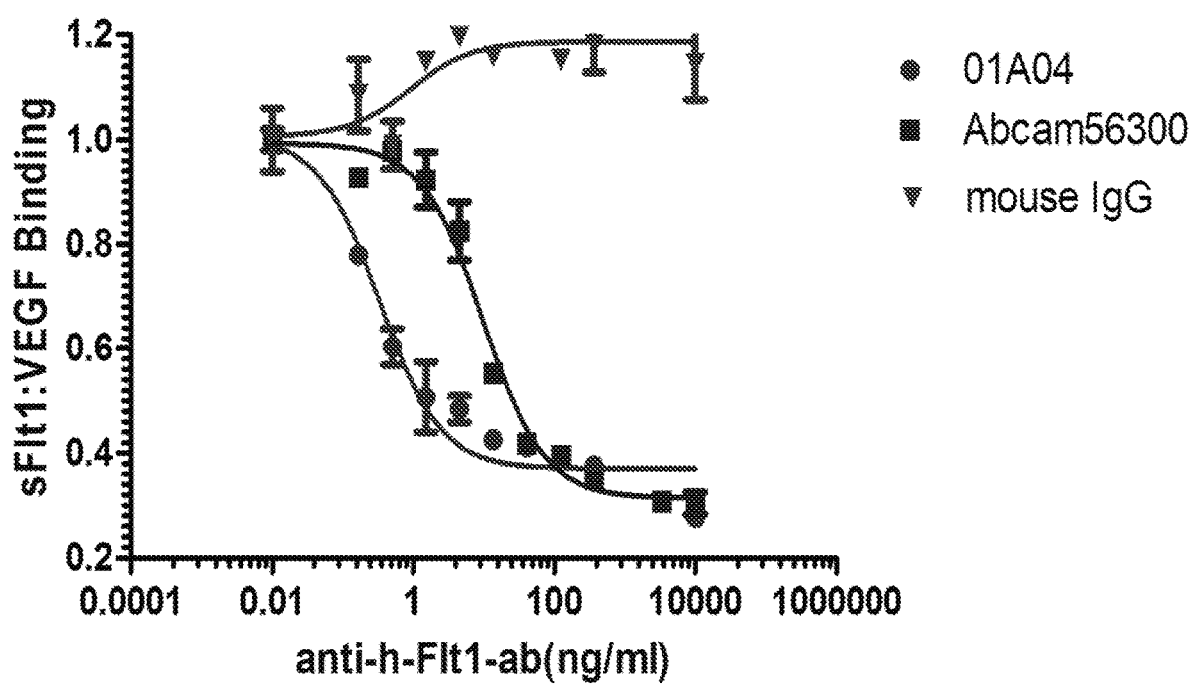
FIG. 6 shows exemplary results illustrating competitive binding of monoclonal antibodies with human soluble Flt-1 in an ELISA. VEGF:sFlt-1 $IC_{50}$ determination of monoclonal antibody 01A04 (sub-clone 02B10-02G07) versus a commercial benchmark is depicted.

To estimate the potency of the antibodies, the competition ELISA (using human sFlt-1 and VEGF) that was set-up for the screening of the llama Fabs and IgGs was used. A concentration range from 10 to 0.01 µg/ml of IgG was tested. Monoclonal antibody 01A04 was assayed versus both negative control (purified polyclonal mouse IgG) and positive control (commercial anti-sFlt-1 monoclonal antibody Abcam56300) molecules. Half maximal inhibition (IC50) values were calculated. Results are presented in FIG. 6.

Antibody 01A04 Characterization—Cell Based Assay

Figure 7:
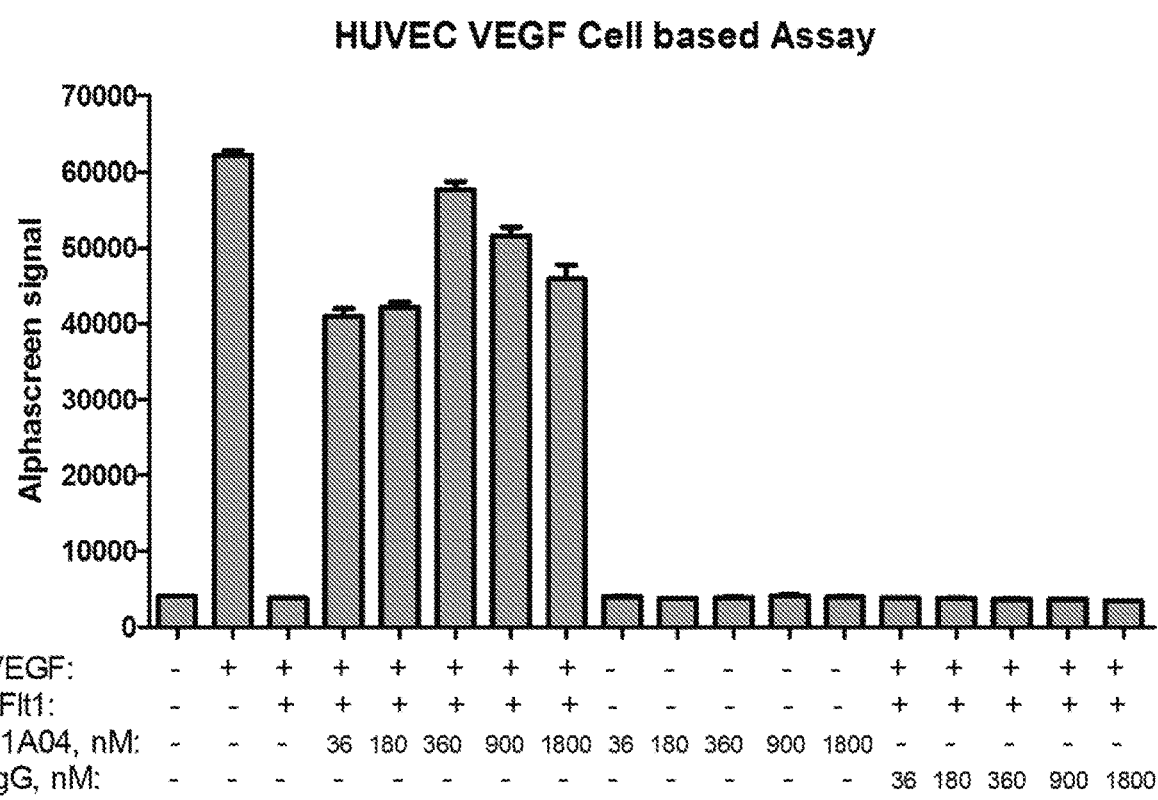
FIG. 7 shows exemplary results illustrating anti-Flt-1 monoclonal antibody inhibition of VEGF binding to sFlt-1 in a cell based assay.

Human primary umbilical vein endothelial cells (HUVECs) were stimulated with VEGF in the presence or absence of soluble Flt-1 and monoclonal antibody 01A04. VEGF induced activation of cells was assayed by determining the phosphorylation status of the VEGF R2 receptor. In the presence of soluble Flt-1, VEGF induced HUVEC activation is attenuated. Addition of monoclonal antibody 01A04 rescues cell activation by antagonizing soluble Flt-1 (FIG. 7).

Example 2. In Vitro Efficacy of Anti-Flt-1 Antibody

Fetal Pulmonary Artery Endothelial Cell Isolation

Pulmonary artery endothelial cells (PAECs) were harvested from the proximal pulmonary arteries of late gestation control fetal sheep at day 135 (day 147 term). Immunohistochemistry with standard endothelial markers confirmed the cell phenotype. Low-passage PAECs (p4-5) were then exposed to ETX, VEGF, sFlt1 or anti-Flt1 alone or in combination.

Growth of PAECs while Exposed to ETX, VEGF, sFlt1 and Anti Flt1

Fetal PAECs were plated in triplicate at 50,000 cells/well in DMEM with 10% FBS into 12 well plates and allowed to adhere overnight in 21% oxygen. The following day (day 0) the cells were washed twice with PBS. DMEM with 2.5% FBS with VEGF, ETX, sFlt1, or anti-Flt1 (alone or in combination) was then added, and cells incubated in 21% oxygen. Final concentrations of exogenous factors were as follows: VEGF 50 ng/mL, ETX 1 ng/mL, sFlt1 114 ng/mL and anti-Flt1 1800 ng/mL. Experimental media was changed daily and cells were counted on day 3 after removing cells with 0.25% trypsin and counted with a cell counter (Beckman Coulter; Fullerton, Calif.). Growth studies with treatment were performed in DMEM with 2.5% FBS, based on previous studies that determined that this was the lowest serum concentration that supported fetal PAEC survival with some proliferation.

PAEC Tube Formation Assay

To assay in vitro angiogenesis, we cross-linked rat-tail collagen using 0.2% Flavin mononucleotide and a UV Stratalinker 1800 (Stratagene). 50,000 cells/well were added in serum free DMEM media supplemented with ETX, VEGF, sFlt1 and anti-Flt1 (alone or in combination) and each condition was tested in triplicate for each animal. PAECs were then incubated for 12-18 hours under 3% oxygen conditions based on previous studies that determined tube formation was more robust in 3% compared to 21% oxygen. Branch-point counting was performed in blinded fashion under ×10 magnification from each of three wells with three to four field of view per well. Wells were imaged using an Olympus IX71 fluorescence microscope (Olympus).

Statistical Analysis

Statistical analysis was performed with the Prism software package (v. 5.0a, GraphPad). Repeated measures one-way analysis of variance (ANOVA) with Bonferroni post-test analysis were performed. P values less than 0.05 were considered significant.

Administration of Anti-Flt-1 Antibody to PAECs Exposed to sFLT

Cells were treated with recombinant human VEGF (50 ng/mL), recombinant human soluble Flt-1 (sFLT, 114 ng/mL) or antibody for human soluble Flt-1 (a-sFLT, 1800 ng/mL) either alone or in combination. PAEC growth was measured 3 days after treatment and the number of tube branch points was measured 24 hours after treatment.

Results

Figure 8:
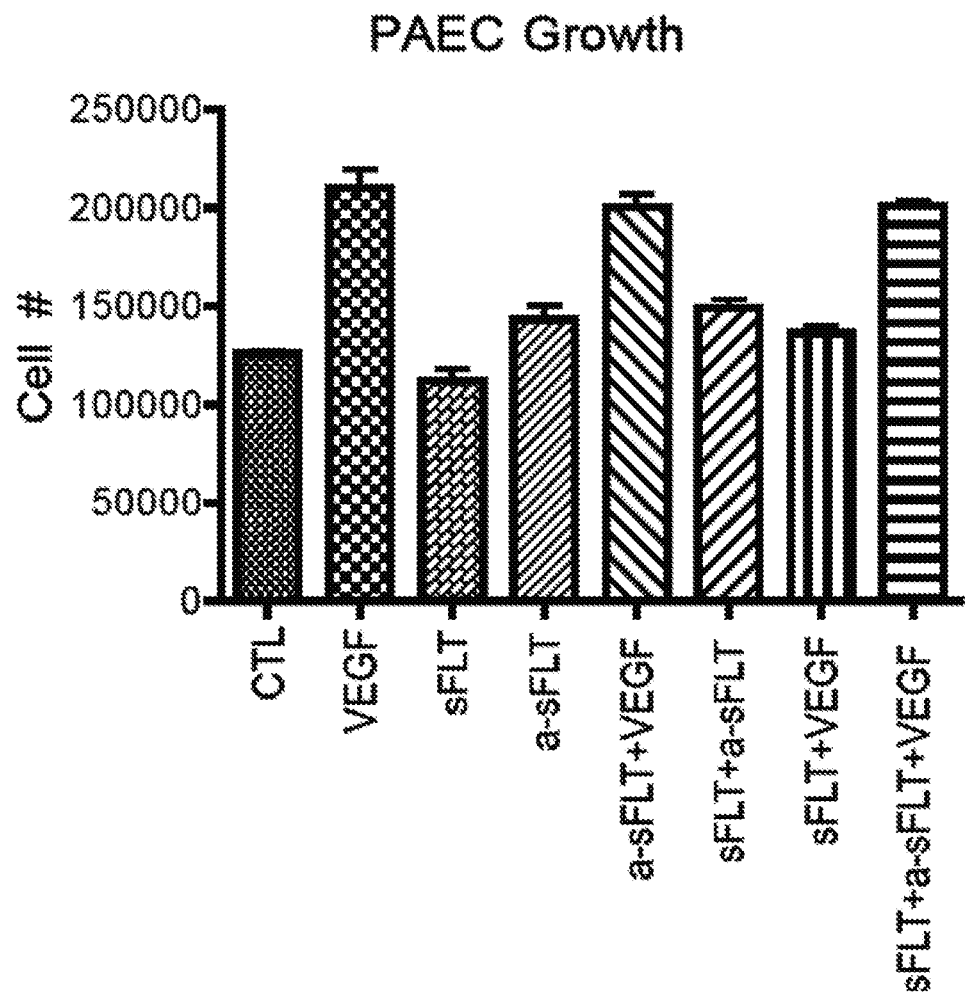
FIG. 8 shows exemplary results illustrating pulmonary artery endothelial cell (PAEC) growth 3 days after treatment.

As shown in FIG. 8, treatment with sFLT and VEGF decreased the number of PAECs compared to cells treated only with VEGF and treatment, indicating that sFLT prevents VEGF from promoting cell growth. When both sFLT and a-sFLT were combined with VEGF, the number of PAECs was brought up to the levels seen when cells were treated with only VEGF, demonstrating that a-sFLT inhibits the sFLT-induced decrease in cell growth.

Figure 10:
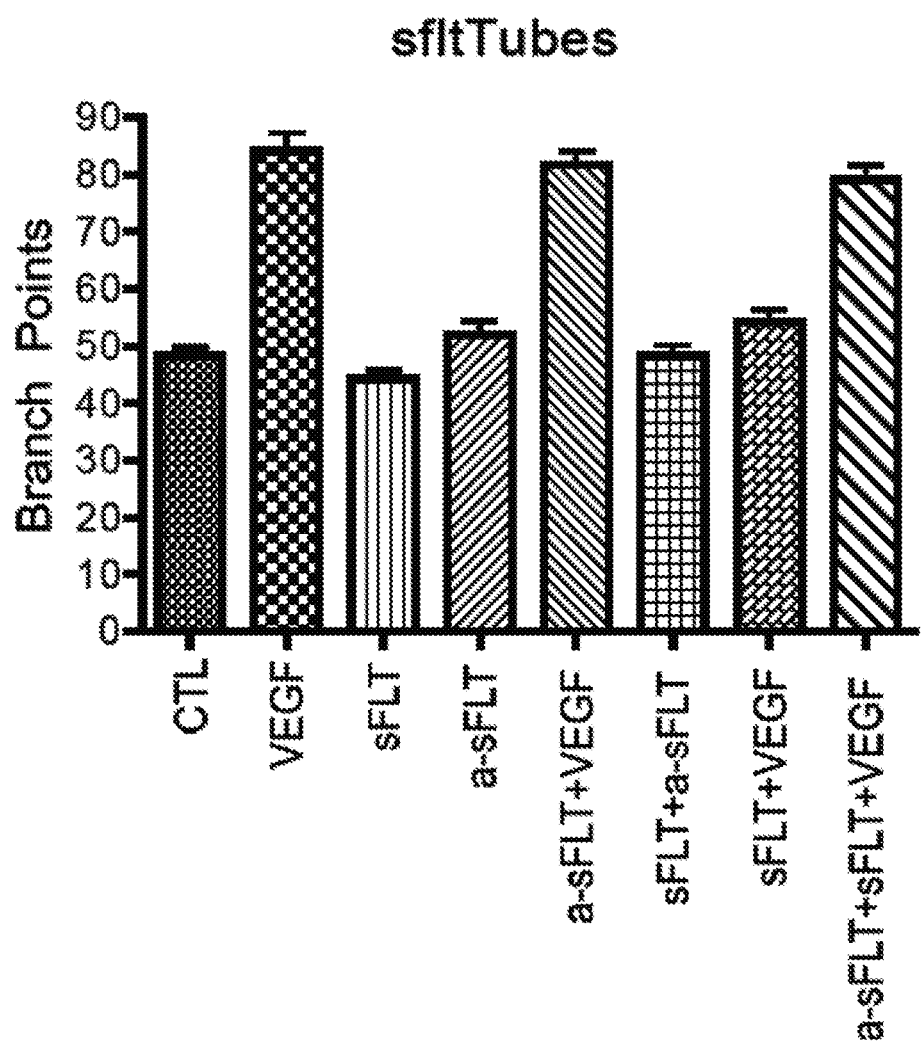
FIG. 10 shows exemplary results illustrating tube formation 24 hours after treatment.

As shown in FIG. 10, treatment with VEGF alone increased the number of tube branch points, as did treatment with VEGF and a-sFLT. Contrastingly, treatment with VEGF and sFLT decreased the number of branch points as compared with the cells treated with only VEGF. When both sFLT and a-sFLT were combined with VEGF, the number of branch points was comparable to the number seen in the VEGF only group, demonstrating that a-sFLT inhibits the sFLT-induced decrease in the number of branch points.

Administration of Anti-Flt-1 Antibody to PAECs Exposed to ETX

Cells were treated with either VEGF (50 ng/mL), endotoxin (ETX, 1 ng/mL), VEGF+ETX, EXT+a-sLFT (1800 ng/mL) or EXT+VEGF+a-sFLT. PAEC growth was measured 3 days after treatment and the number of tube branch points was measured 24 hours after treatment.

Results

Figure 9:
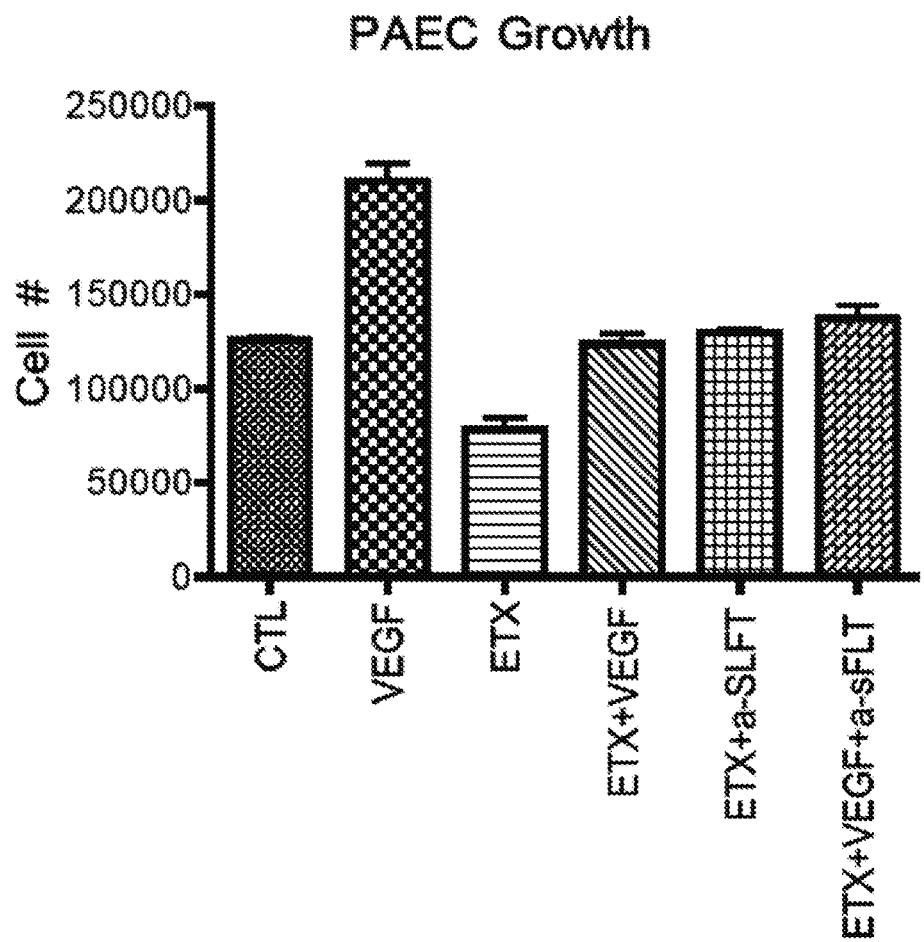
FIG. 9 shows exemplary results illustrating PAEC growth 3 days after treatment.

As shown in FIG. 9, PAEC growth was increased after treatment with VEGF compared to control (CTL) and PAECs treated with only ETX showed decreased growth compared to control. The combination of either VEGF or a-sFLT with ETX brought cells numbers up to the level seen in the control group, as did treatment with ETX, VEGF and a-sFLT, demonstrating that treatment with either VEGF or a-sFLT can reverse the detrimental effects of ETX on PAEC growth.

Figure 11:
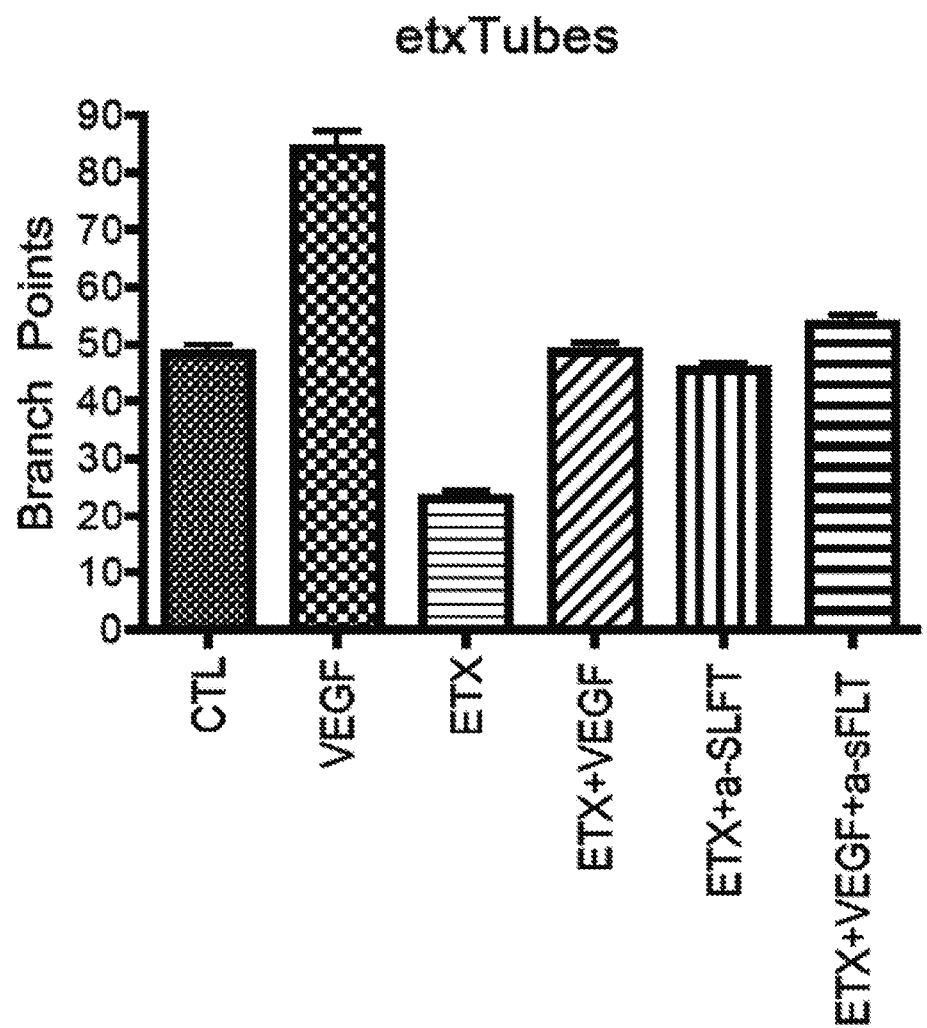
FIG. 11 shows exemplary results illustrating tube formation 24 hours after treatment.

As shown in FIG. 11, the number of branch points increased after treatment with VEGF only and cells treated with only ETX showed a decreased number of branch points compared to both the control and VEGF treated groups. The combination of either VEGF or a-sFLT with ETX brought the number of branch points up to the level seen in the control group, as did treatment with ETX, VEGF and a-sFLT, demonstrating that treatment with either VEGF or a-sFLT can reverse the detrimental effects of ETX on the number of branch points in tubes.

Example 3. In Vivo Efficacy of Anti-Flt-1 Antibody in ETX Model of BPD

Animals

All procedures and protocols were approved by the Animal Care and Use Committee at the University of Colorado Health Sciences Center. Timed pregnant Sprague-Dawley rats were purchased from Charles River Laboratories (Wilmington, Mass.) and maintained in room air at Denver's altitude (1,600 m; barometric pressure, 630 mmHg; inspired oxygen tension, 122 mmHg) for at least 1 week before giving birth. Animals were fed ad libitum and exposed to day-night cycles alternatively every 12 hours. Rats were killed with an intraperitoneal injection of pentobarbital sodium (0.3 mg/g body weight; Fort Dodge Animal Health, Fort Dodge, Iowa).

Animal Model and Study Design

Intra-Amniotic ETX, Vitamin D and Anti-sFLT Administration

An animal model of chorioamnionitis was utilized. At 20 days gestation (term: 22 days), pregnant rats were prepared for receiving intra-amniotic (IA) injections. The timing of injection during the late canalicular stage of lung development in the rat was selected to parallel the similar stage of human lung development in 24 to 26 week premature newborns who are at the highest risk for BPD. After pre-medication with buprenorphine (0.01-0.05 mg/kg, subcutaneous injection), laparotomy was performed under general anesthesia with 1-2% isoflurane inhalation via facemask (anesthesia machine: Matrx by Midmark, model VIP3000). During anesthesia and laparotomy, pregnant rats were kept on a heating pad for preventing hypothermia. Pregnant rats were randomly assigned to saline control (CTR), endotoxin (ETX), or ETX+vitamin D (vit D) group in one study or to saline control (CTR), endotoxin (ETX) or ETX+anti-sFLT in the other study. The CTR groups received 50 µl of normal 136 saline per amniotic sac, the ETX groups received 10 µg of *Escherichia coli* 055:B55 ETX (Sigma Chemical, St. Louis, Mo.) diluted to 50 µl with normal saline per sac, the ETX+vit D group received 10 µg of *Escherichia coli* 055:B55 ETX and 50 pg diluted to 50 µl with normal saline and the ETX+anti-sFLT group received 10 µg of *Escherichia coli* 055:B55 ETX and low dose (lx molar equivalent) or high dose (10× molar equivalent) anti-sFlt1 antibody. Under sterile preparation, a midline abdominal incision of 3-4 cm in length was made to expose the amniotic sacs for IA injections. The amniotic sac closest to the right ovary was first identified and injected, and then in a counterclockwise sequence each sac was identified and injected with a maximum of 10 sacs injected per dam. Injections were limited to 10 sacs to prevent maternal mortality due to systemic toxicities from accumulating doses of IA ETX. The dose of ETX was established from previous studies that demonstrated ETX at lower doses (1-5 µg/sac) failed to induce abnormal lung structure at 14 days of age. The dose of vit D was established again from previous studies demonstrating vit D at higher doses (500 ng/gm) produced subcutaneous calcium deposits noted in rat pups. The abdominal incision was closed with nylon sutures. Bupivacaine (1-2 mg/kg, intramuscular injection) was applied over the incision wound for postoperative pain control. Pregnant rats were monitored closely to ensure arousal within 10 minutes after surgery, and rats were placed back to the cages and were monitored for activity and for signs of bleeding or infection.

Cesarean Section

Two days after IA injections, cesarean section was performed on pregnant rats under general anesthesia with isoflurane inhalation, as described above. The fetus in the amniotic sac closest to the right ovary was first delivered, which was followed by delivery of the rest of the fetuses in a counterclockwise sequence, to identify fetuses exposed to IA injections. Cesarean sections were performed instead of allowing vaginal deliveries in order to identify fetuses exposed to specific IA injections, based on the order of the amniotic sacs and their anatomic locations related to the ovaries. All of the rat pups in the injected amniotic sacs were delivered within 5 minutes after onset of anesthesia. Mother rats were then euthanized with pentobarbital sodium. Newborn rats were immediately dried and placed on a heating pad to avoid hypothermia. Pups received no supplemental oxygen or artificial ventilation at birth. Within 30 minutes after birth, pups were weighed and either sacrificed for histology or placed with foster mother rats to be raised through 14 days. Rat lungs were harvested at birth and 14 days of age for histological assessment. Survival of the infant rats was monitored and recorded daily from birth throughout the study period. Survival rate was calculated as the number of survived pups divided by the number of sacs that received intra-amniotic injection in each given litter.

Study Measurements

Tissue for Histological Analysis

Animals were killed with intra-peritoneal pentobarbital sodium. A catheter was placed in the trachea and the lungs were inflated with 4% paraformaldehyde and maintained at 20 cm $H_2O$ pressure for 60 minutes. A ligature was tightened around the trachea to maintain pressure and the tracheal cannula was removed. Lungs were immersed in 4% paraformaldehyde at room temperature overnight for fixation. A 2-mm thick transverse section was taken from the mid-plane of right lower lobe and left lobe of the fixed lungs per animal, respectively. Two sections from each animal were processed and embedded in paraffin wax for study.

Bronchoalveolar Lavage (BAL)

Bronchoalveolar lavage was performed on the day of birth (Day 0) according to standard techniques and sFLT levels in the lung were measured.

Radial Alveolar Counts (RAC)

Alveolarization was assessed by the RAC method of Emery and Mithal as described (Cooney T P, Thurlbeck W M. The radial alveolar count method of Emery and Mithal: a reappraisal 1—postnatal lung growth. Thorax 37: 572-579, 1982; Cooney T P, Thurlbeck W M. The radial alveolar count method of Emery and Mithal: a reappraisal 2—intrauterine and early postnatal lung growth. Thorax 37: 580-583, 1982). Respiratory bronchioles were identified as bronchioles lined by epithelium in one part of the wall. From the center of the respiratory bronchiole, a perpendicular line was dropped to the edge of the acinus connective tissues or septum or pleura, and the number of septae intersected by this line was counted.

Statistical Analysis

Statistical analysis was performed with the Prism software package (v. 5.0a, GraphPad). Repeated measures one-way analysis of variance (ANOVA) with Bonferroni post-test analysis were performed. P values less than 0.05 were considered significant.

Results

Figure 12:
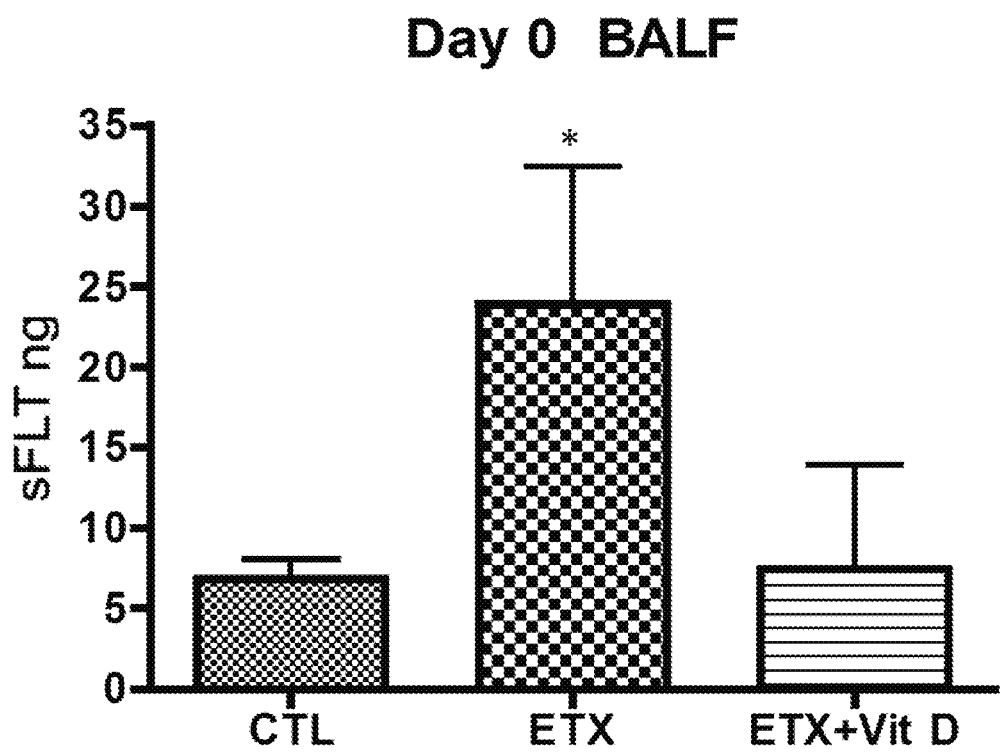
FIG. 12 shows exemplary results illustrating the effects of in utero dosing of Vitamin D in an endotoxin (ETX) induced model of BPD in rats.

As shown in FIG. 12, sFLT levels were significantly (* p<0.05) increased in rats exposed to ETX in utero compared to the control group and treatment with Vitamin D decreased the levels of sFLT to the level seen in the control group. This demonstrates that treatment with Vitamin D could be used as a therapeutic for treating BPD via the action of Vitamin D on levels of sFLT in the lungs.

Figure 13:
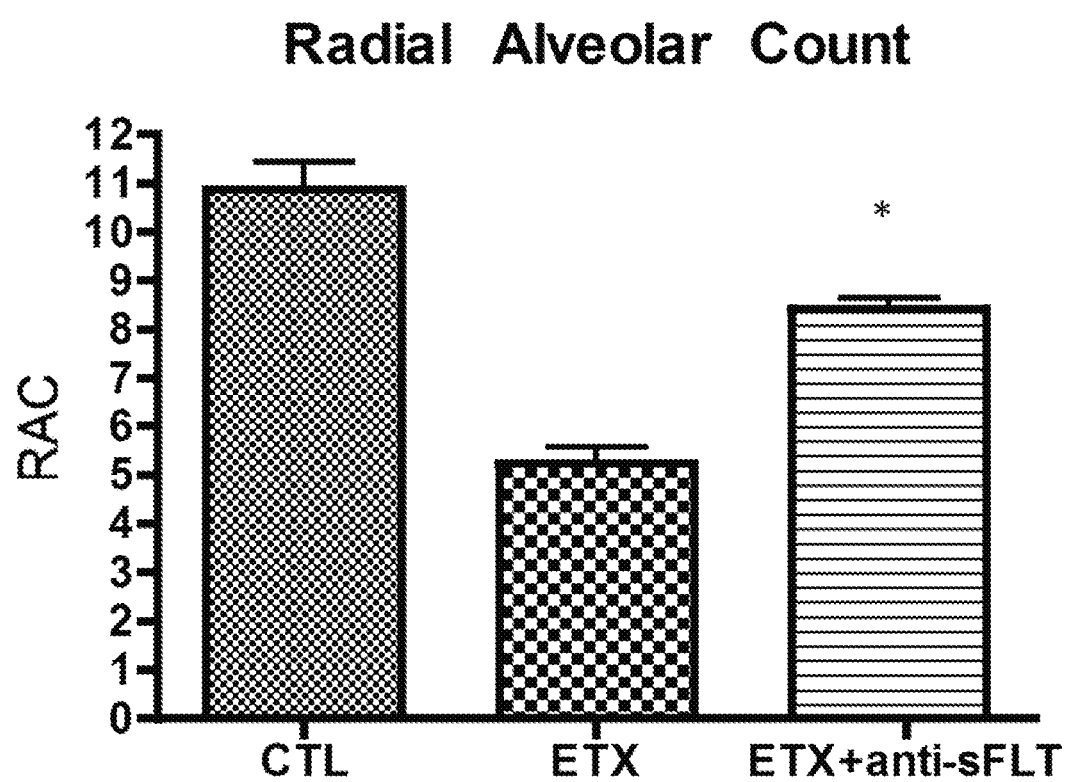
FIG. 13 shows exemplary results illustrating the effects of in utero dosing of anti-Flt-1 monoclonal antibody in an endotoxin (ETX) induced model of BPD in rats.

As shown in FIG. 13, by morphometric analysis, RAC was decreased in rats exposed to ETX in utero compared to the control group and in utero dosing with anti-sFLT in rats exposed to ETX significantly (* p<0.05) increased RAC compared to the group only exposed to ETX. This demonstrates that treatment with anti-sFLT could be used as a therapeutic for treating BPD.

Example 4. In Vivo Efficacy of Anti-Flt-1 Antibody in sFLT Model of BPD

Animals

All procedures and protocols were approved by the Animal Care and Use Committee at the University of Colorado Health Sciences Center. Pregnant Sprague-Dawley rats were purchased from Charles River Laboratories (Wilmington, Mass.) and maintained in room air at Denver's altitude (1,600 meters; barometric pressure, 630 mmHg; inspired oxygen tension, 122 mmHg) for at least 1 week before giving birth. Animals were fed ad libitum and exposed to day-night cycles alternatively every 12 hours. Rats were killed with an intraperitoneal injection of pentobarbital sodium (0.3 mg/g body wt; Fort Dodge Animal Health, Fort Dodge, Iowa).

Study Design

Intra-Amniotic sFlt-1 Administration

At 20 days gestation (term: 22 days), pregnant rats were prepared for receiving intra-amniotic injections. The timing of injection during the late canalicular stage of lung development in the rat was selected to parallel a similar stage of human lung development in 24- to 26-week premature newborns who are at the highest risk for BPD. After premedication with buprenorphine (0.01-0.05 mg/kg, intramuscular injection), laparotomy was performed on pregnant rats under general anesthesia with 1-2% isoflurane inhalation via a face mask (Anesthesia machine: Matrx by Midmark, model VIP3000). During anesthesia and laparotomy, pregnant rats were kept on a heating pad for preventing hypothermia. Pregnant rats were randomly assigned to saline control or sFlt-1 group; the saline group received 50 μL of normal saline per amniotic sac, and the sFlt-1 groups received 50 μg of recombinant human sFlt-1-Fc (R&D Systems, Minneapolis, Minn.) diluted to 50 μL with normal saline per sac. One sFLT group received a low dose (lx molar equivalent) of anti-sFLT and the other received a high dose (10× molar equivalent) of anti-sFLT. Under sterile preparation, a midline abdominal incision of 3-4 cm in length was made to expose the amniotic sacs for intra-amniotic injections. The amniotic sac closest to the right ovary was first identified and injected, and then in a counterclockwise sequence each sac was identified and injected with a maximum of 10 sacs injected per dam. Limiting sFlt-1 injections to 10 sacs per pregnant rat was to achieve a consistent total dose of sFlt-1 on the individual mother rats, given intra-amniotic sFlt-1 is absorbed into the maternal circulation through an intramembranous pathway, which is characterized by a microscopic network of fetal vasculature on the fetal surface of the placenta to mediate the transfer of intraamniotic substances into fetal and maternal circulations. Similarly, considering the communication between the amniotic cavity and maternal and fetal circulations through the intramembranous pathway, intra-amniotic saline was given in separate litters to serve as controls. The total number of amniotic sacs in each mother rat was examined and recorded during laparotomy. The abdominal incision was closed with nylon sutures. Bupivacaine (1-2 mg/kg, subcutaneous injection) was applied over the incision wound for postoperative pain control. Pregnant rats were monitored closely to ensure arousal within 10 minutes after surgery, and rats were placed back to the cages and were monitored for activity, ability to drink and eat, and for signs of bleeding or infection.

Cesarean Section

Two days after intra-amniotic injections, cesarean section was performed on pregnant rats under general anesthesia with isoflurane inhalation, as described above. The fetus in the amniotic sac closest to the right ovary was first delivered, which was followed by delivery of the rest of the fetuses in a counterclockwise sequence, to identify fetuses exposed to intra-amniotic injections. The total number of amniotic sacs in each mother rat was further verified at the time of delivery. The main reason for performing cesarean section instead of allowing vaginal delivery is to identify the fetuses exposed to intra-amniotic injections, based on the order of the amniotic sacs and their anatomic locations related to the ovaries. All of the rat pups in the injected amniotic sacs were delivered within 5 minutes after the onset of anesthesia. Maternal rats were then killed with pentobarbital sodium. Newborn rats were immediately placed on a heating pad to avoid hypothermia and were dried manually with gauze sponges. Pups received no supplemental oxygen or artificial ventilation at birth. The survival rate at birth was recorded. Within 30 minutes after birth, the pups were weighed and placed with foster mother rats in regular cages. For the first 24 h of life, the newborn pups were monitored closely for mortality or signs of respiratory distress.

Rat lungs were harvested at birth for Western blot analysis and at birth and 14 days of age for histological assessment. Hearts were dissected and weighed at birth and 7 and 14 days of age. Three to nine rats were studied in each group for each measurement at each time point. Survival of the infant rats was monitored and recorded daily from birth throughout the study period. Survival rate was calculated as the number of survived pups divided by the number of sacs that received intra-amniotic injection in each given litter. Body weight was measured at birth and at the time of being killed for study measurements.

Study Measurements

Tissue for Histological Analysis

Animals were killed with intraperitoneal pentobarbital sodium. A catheter was placed in the trachea, and the lungs were inflated with 4% paraformaldehyde and maintained at 20 cm $H_2O$ pressure for 60 min. A ligature was tightened around the trachea to maintain pressure, and then the tracheal cannula was removed. Lungs were then immersed in 4% paraformaldehyde at room temperature for 24 hours for fixation. A 2-mm-thick transverse section was taken from the midplane of the right lower lobe and left lobe of the fixed lungs per animal, respectively, to process and embed in paraffin wax.

Immunohistochemistry

Slides with 5 μm paraffin sections were stained with hematoxylin and eosin for assessing alveolar structures and with von Willebrand Factor (vWF), an endothelial cell-specific marker, for quantifying vessel density.

Pulmonary Vessel Density

Pulmonary vessel density was determined by counting vWF-stained vessels with an external diameter at 50 μm or less per high-power field. The fields containing large airways or vessels with external diameter >50 μm were avoided.

Radial Alveolar Counts (RAC)

Alveolarization was assessed by the RAC method of Emery and Mithal as described (Cooney T P, Thurlbeck W M. The radial alveolar count method of Emery and Mithal: a reappraisal 1—postnatal lung growth. Thorax 37: 572-579, 1982; Cooney T P, Thurlbeck W M. The radial alveolar count method of Emery and Mithal: a reappraisal 2—intrauterine and early postnatal lung growth. Thorax 37: 580-583, 1982). Respiratory bronchioles were identified as bronchioles lined by epithelium in one part of the wall. From the center of the respiratory bronchiole, a perpendicular line was dropped to the edge of the acinus connective tissues or septum or pleura, and the number of septae intersected by this line was counted.

Indices of Right Ventricular Hypertrophy

The right ventricle (RV) and left ventricle plus septum (LV+S) were dissected and weighed. The ratios of RV to LV+S weights (RV/LV+S %) and RV/body weights (RV/BW %) were determined to evaluate right ventricular hypertrophy (RVH).

Statistical Analysis

Statistical analysis was performed with the InStat 3.0 software package (GraphPad Software, San Diego, Calif.). Statistical comparisons were made between groups using t-test or ANOVA with Newman-Keuls post hoc analysis for significance. $P<0.05$ was considered significant.

Results

Figure 14:
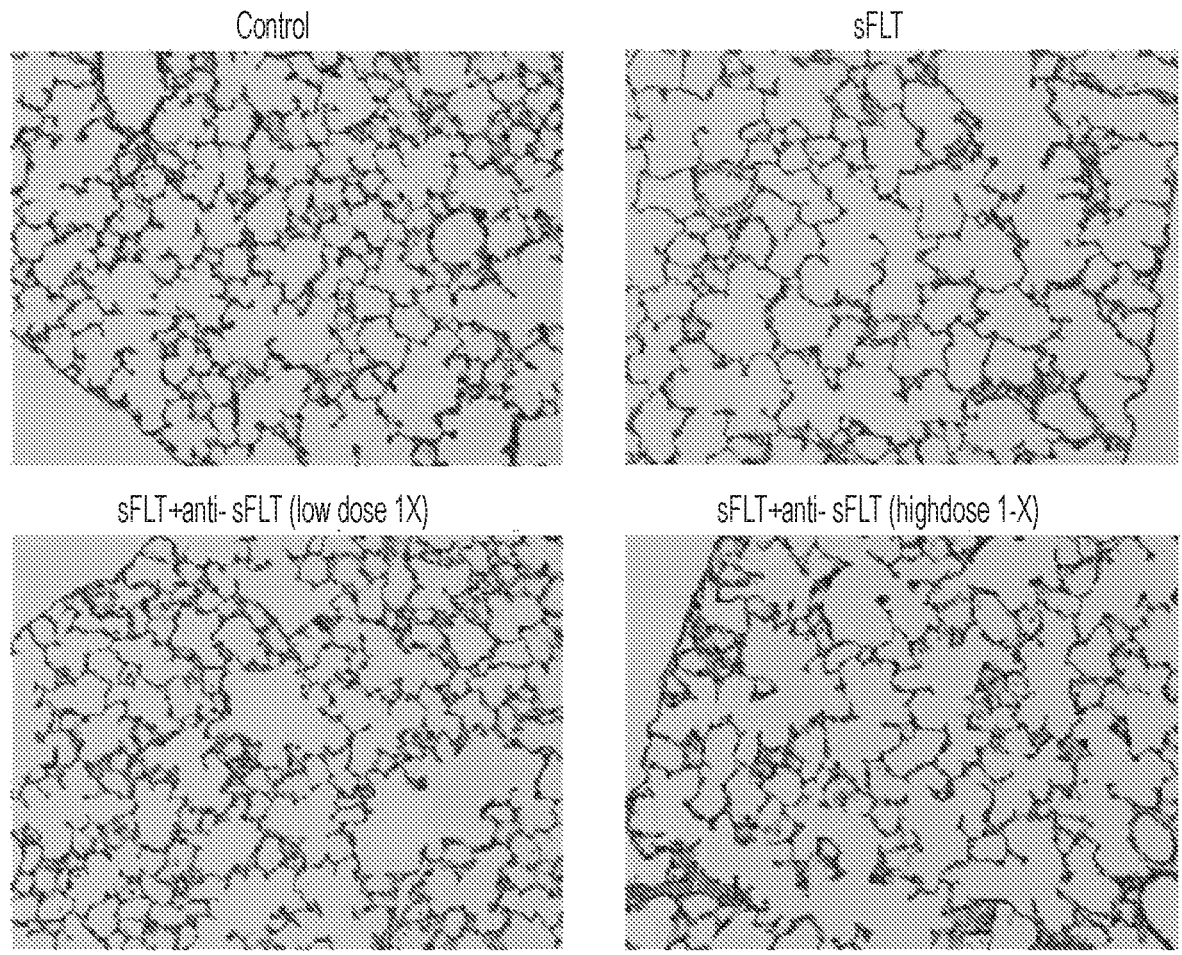
FIG. 14 shows exemplary results illustrating the effects of in utero dosing of anti-Flt-1 monoclonal antibody in a soluble Flt1 (sFLT) induced model of BPD on pulmonary vessel density in rats.
Figure 15:
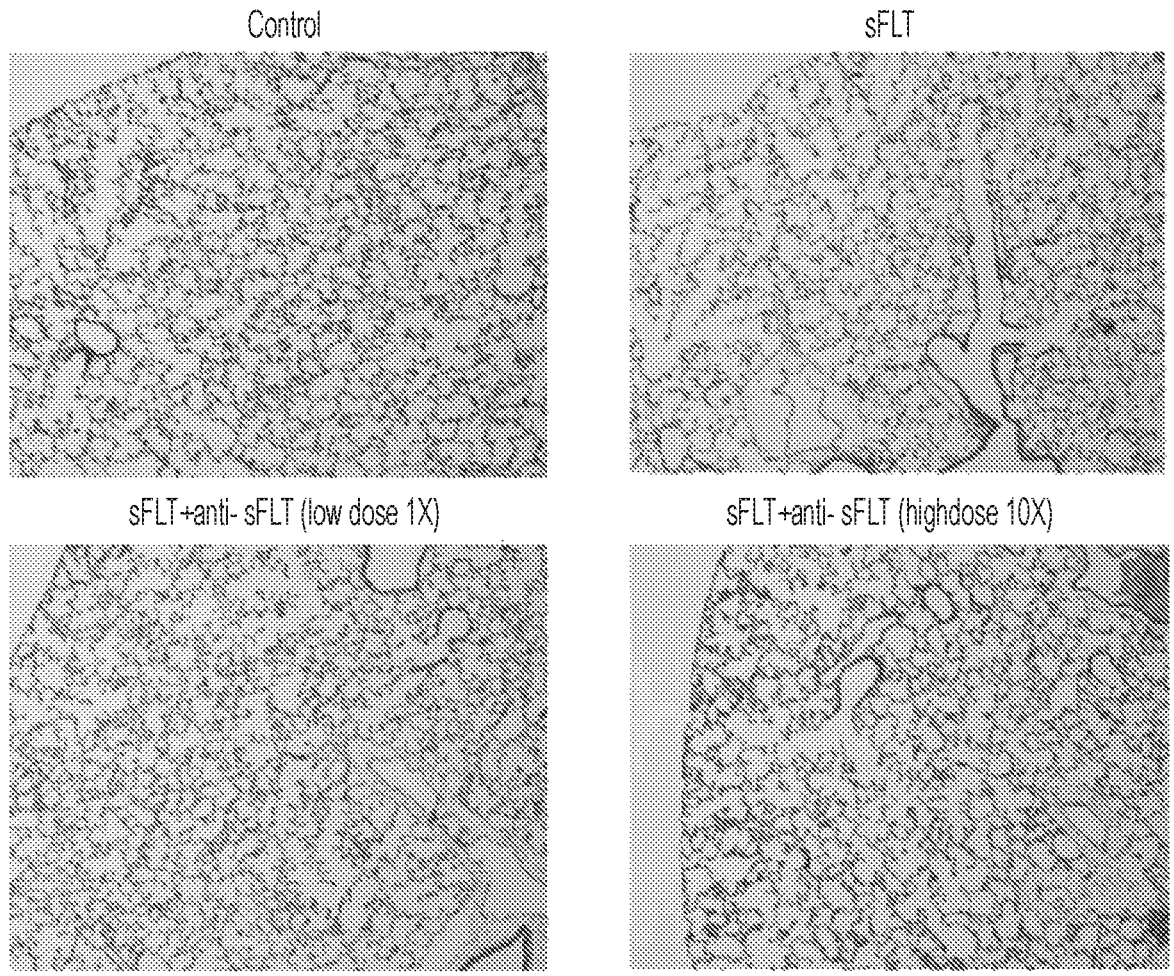
FIG. 15 shows exemplary results illustrating the effects of in utero dosing of anti-Flt-1 monoclonal antibody in a soluble Flt1 (sFLT) induced model of BPD on pulmonary vessel density in rats.

As shown in FIGS. 14 and 15, pulmonary vessel density was increased in animals treated with sFLT+anti-sFLT compared to those treated only with sFLT.

Figure 16:
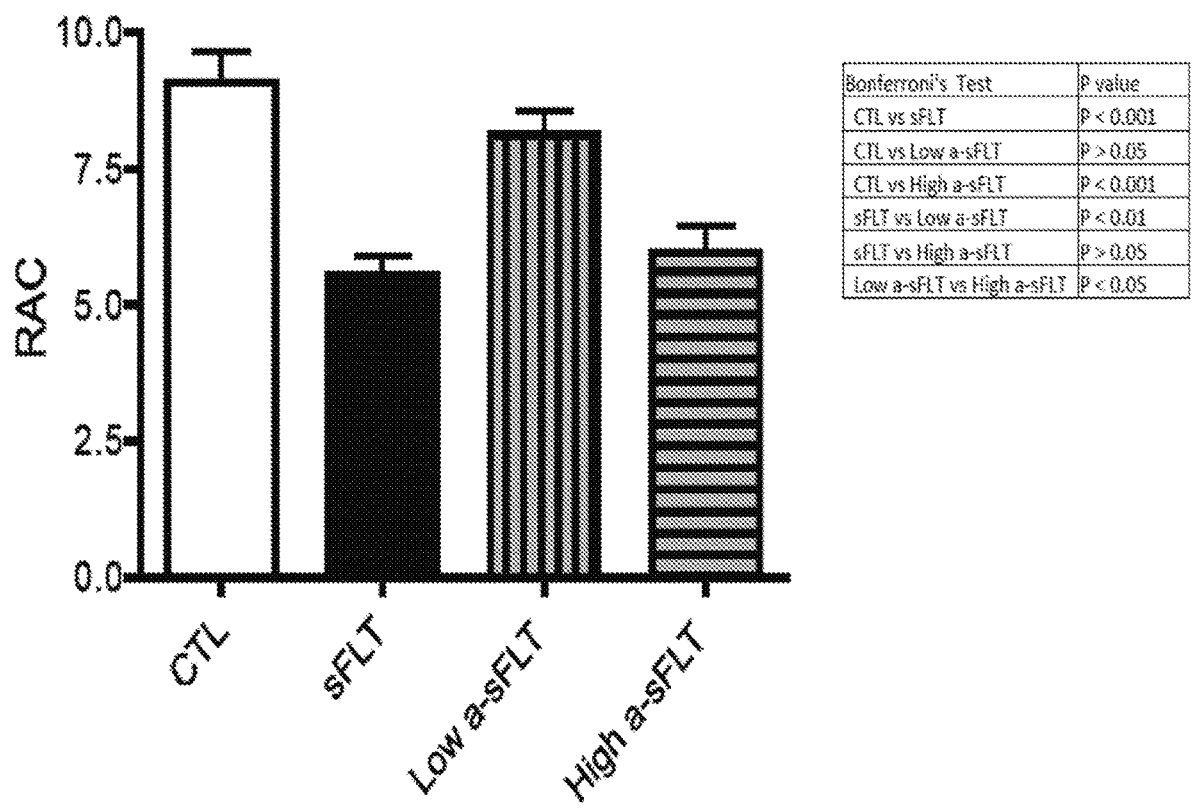
FIG. 16 shows exemplary results illustrating the effects of low and high doses of anti-Flt-1 monoclonal antibody (a-sFLT) in a soluble Flt1 (sFLT) induced model of BPD in rats.

Alveolarization was assessed by the radial alveolar count (RAC) method. As shown in FIG. 16, when analyzed by morphometric analysis, sFLT rats had significantly ($P<0.001$) decreased RAC compared with the control group (CTL). Treatment with the low dose of a-sFLT significantly ($P<0.01$) increased RAC compared to the sFLT group. This indicates that treatment with a-sFLT can reverse the decrease in alveolarization caused by sFLT.

Figure 17:
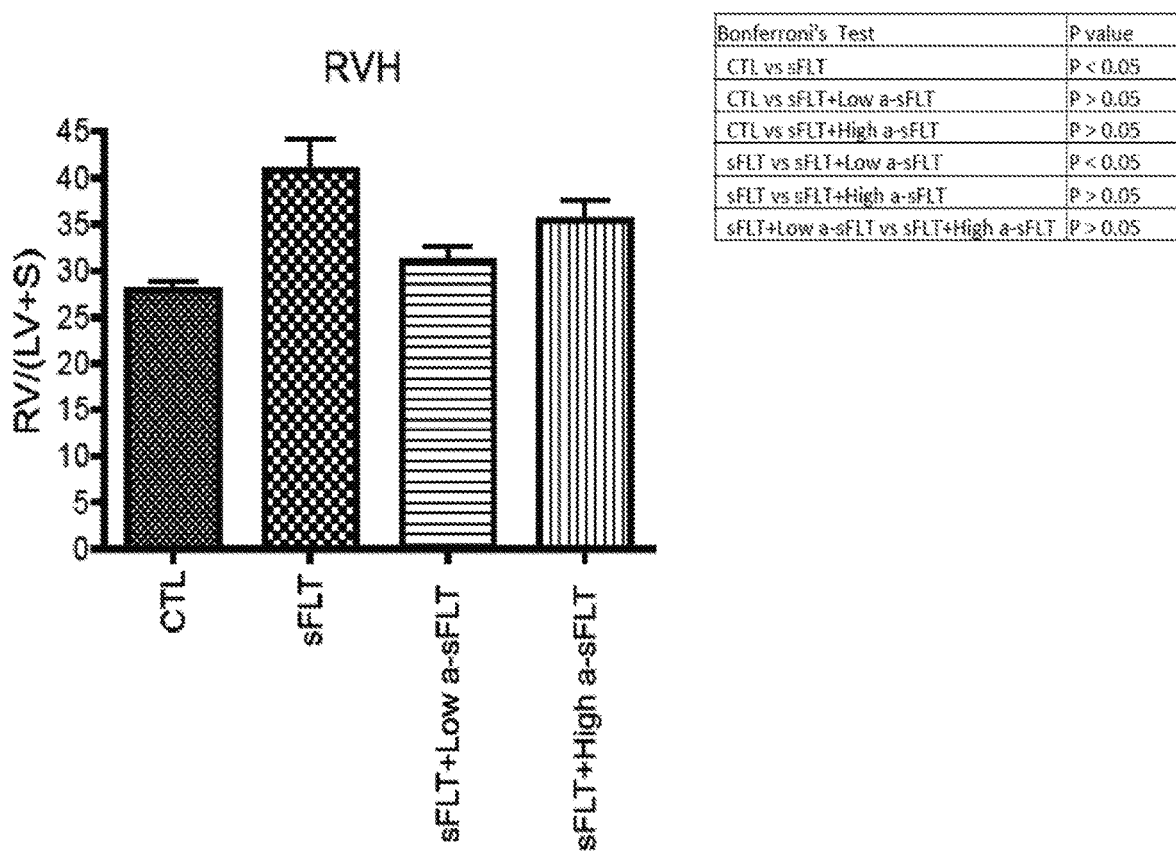
FIG. 17 shows exemplary results illustrating the effects of low and high doses of anti-Flt-1 monoclonal antibody (a-sFLT) in a soluble Flt1 (sFLT) induced model of BPD in rats.

Right ventricular hypertrophy was assessed by weighing the right ventricle (RV) and left ventricle plus septum (LV+S) and calculating the ratio. As shown in FIG. 17, animals exposed to sFLT had a significantly increased ($P<0.05$) RV/(LV+S) ratio compared to the control group. Treatment with the low dose of a-sFLT significantly ($P<0.05$) decreased the RV/(LV+S) ratio compared to the sFLT group. This indicates that treatment with a-sFLT can reverse the right ventricular hypertrophy caused by sFLT.

Figure 18:
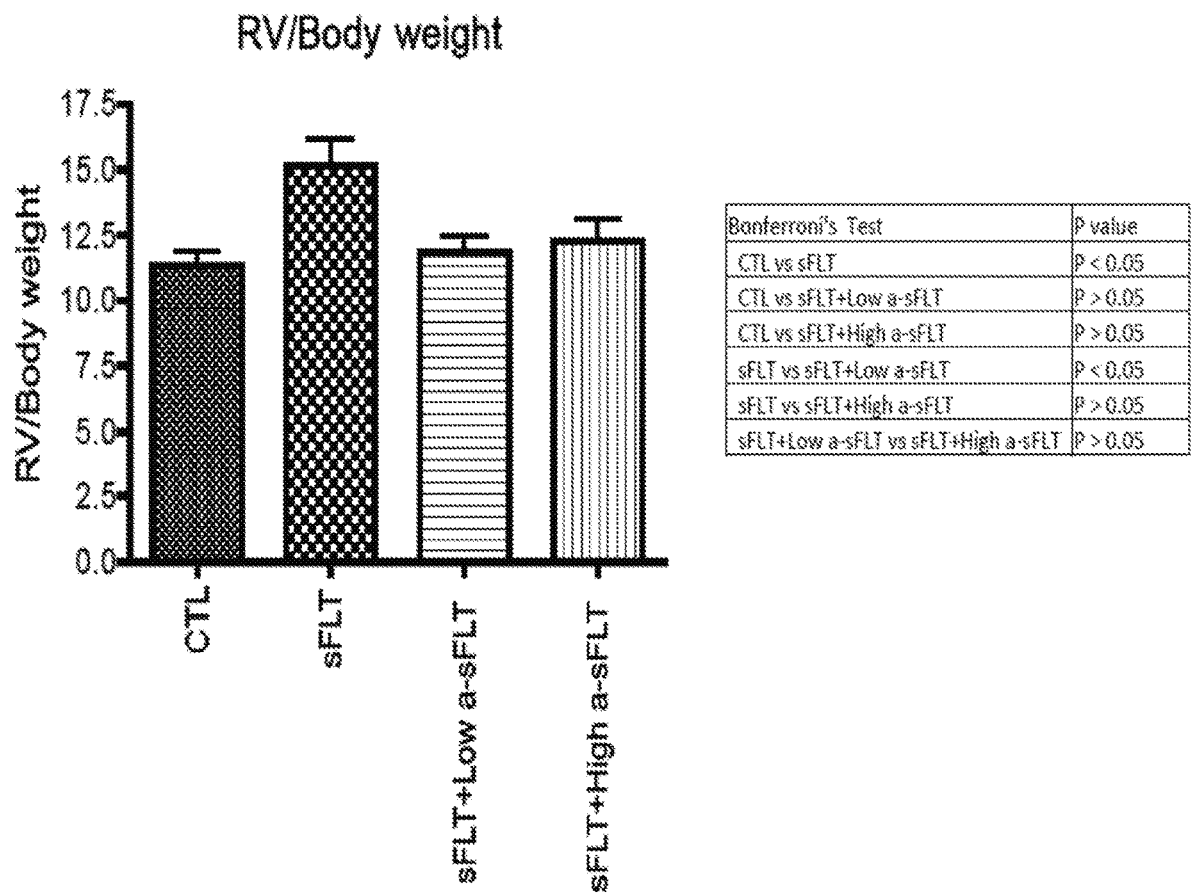
FIG. 18 shows exemplary results illustrating the effects of low and high doses of anti-Flt-1 monoclonal antibody (a-sFLT) in a soluble Flt1 (sFLT) induced model of BPD in rats.

The ratio of the right ventricle (RV) to body weight was determined to evaluation right ventricular hypertrophy. As shown in FIG. 18, animals exposed to sFLT had a significantly ($P<0.05$) increased RV/body weight ratio compared to the control group. Treatment with the low dose of a-sFLT significantly decreased the RV/body weight ratio ($P<0.05$) compared to the sFLT group. This indicates that treatment with a-sFLT can reverse the right ventricular hypertrophy caused by sFLT.

Example 5. In Vivo Efficacy of Anti-Flt-1 Antibody in an Endotoxin (ETX) Model of BPD Study Design Intra-Amniotic sFlt-1 and ETX Administration At 20 days gestation (term: 22 days), pregnant rats were prepared for receiving intra-amniotic injections. Pregnant rats were randomly assigned to saline control or ETX (endotoxin) group; the saline group received normal saline injection into the amniotic sac, and the and the ETX groups received 10 μg endotoxin per sac. Following intra-amniotic administration, the abdominal incision was closed and rats were monitored closely to ensure arousal after surgery.

Cesarean Section and Treatment

Two days after intra-amniotic injections, cesarean section was performed on pregnant rats under general anesthesia, as described above. Pups were treated twice a week for two weeks with 1 mg/kg anti-sFLT monoclonal, 10 mg/kg anti-sFLT monoclonal or 10 mg/kg IgG control (mouse IgG1 isotype control).

Study Measurements

At day 14, rat lungs were harvested for morphometric analysis and for histological assessment. Body weight of the animals was measured at birth and at the time of sacrifice. Lungs were fixed after inflation with 4% paraformaldehyde at 20 cm $H_2O$. Distal airspace structure was assessed by Radial Alveolar Counts (RAC). Hearts were collected to determine right ventricular hypertrophy (RV/LS+S weights)

Body Weight

Figure 19:
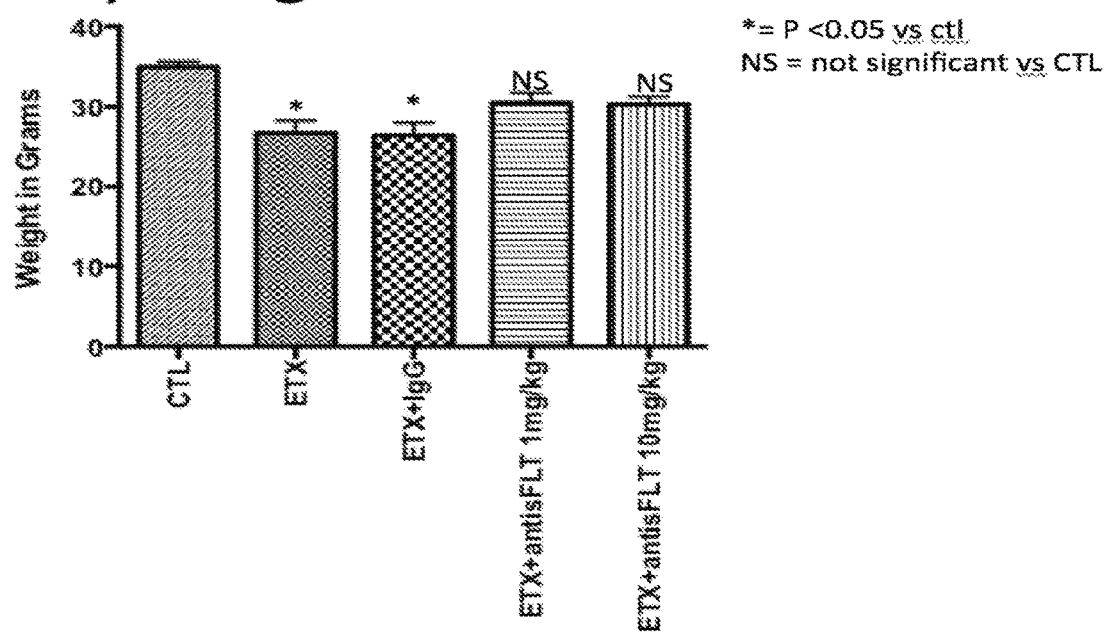
FIG. 19 shows exemplary results illustrating the effects of 1 mg/kg and 10 mg/kg postnatal doses of anti-Flt-1 monoclonal antibody (antisFLT) on body weight in an endotoxin (ETX) induced model of BPD in rats.

The body weight of animals was measured to determine if postnatal anti-Flt-1 monoclonal antibody treatment improved body weight following antenatal ETX treatment. Animals administered ETX in utero followed by postnatal treatment with IgG (control) or anti-Flt-1 mAb (1 mg/kg or 10 mg/kg) were weighed. Animals receiving only ETX or ETX+IgG weighed significantly less than control animals (FIG. 19). The weight of animals receiving ETX+either dose of anti-Flt-1 mAb was not significantly different from the weight of control animals. These data indicate that animals given postnatal anti-Flt-1 mAb have a growth advantage in an endotoxin induced model of BPD.

Radial Alveolar Counts (RAC)

Figure 20:
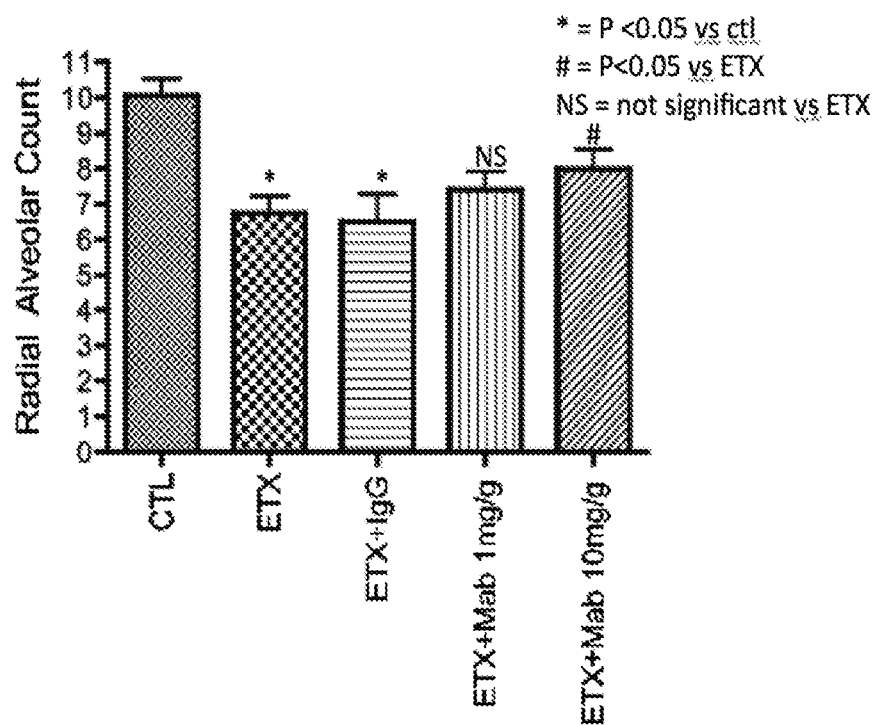
FIG. 20 shows exemplary results illustrating the effects of 1 mg/kg and 10 mg/kg postnatal doses of anti-Flt-1 monoclonal antibody (Mab) on radial alveolar count (RAC) in an endotoxin (ETX) induced model of BPD in rats.

Radial alveolar count was measured to determine if postnatal anti-Flt-1 monocolonal antibody treatment improved alveolar growth after antenatal ETX treatment. The lungs of animals administered ETX in utero followed by postnatal treatment with IgG (control treatment) or anti-Flt-1 monoclonal antibody (1 mg/kg or 10 mg/kg) were studied. Animals receiving only ETX or ETX+IgG demonstrated significantly reduced alveolar growth as compared to control animals (FIG. 20). Alveolar growth in animals receiving ETX+10 mg/kg of anti-Flt-1 monoclonal antibody was significantly better than alveolar growth in animals receiving ETX alone. These data indicate that animals given postnatal anti-Flt-1 monoclonal antibody have improved lung structure in an endotoxin induced model of BPD.

Indices of Right Ventricular Hypertrophy

Figure 21:
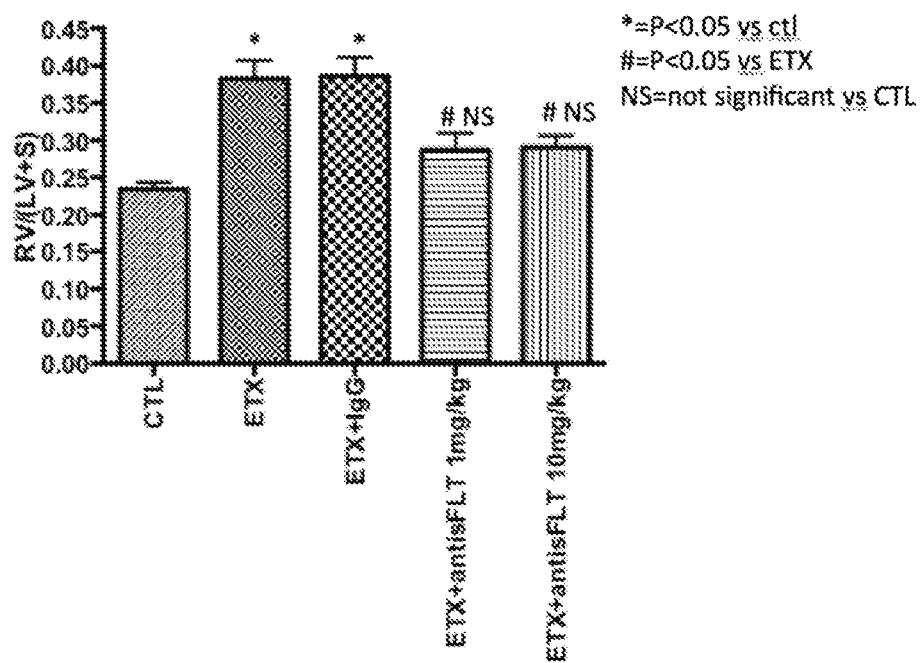
FIG. 21 shows exemplary results illustrating the effects of 1 mg/kg and 10 mg/kg postnatal doses of anti-Flt-1 monoclonal antibody (antisFLT) on right ventricular hypertrophy (RVH) in an endotoxin (ETX) induced model of BPD in rats.

The right ventricle was measured to determine if postnatal anti-Flt-1 monoclonal antibody treatment prevented right ventricular hypertrophy (RVH) after antenatal ETX treatment. The hearts of animals administered ETX in utero followed by postnatal treatment with IgG (control treatment) or anti-Flt-1 monoclonal antibody (1 mg/kg or 10 mg/kg) were studied. Animals receiving only ETX or ETX+IgG demonstrated a significantly increased right ventricle ratio as compared to control animals (FIG. 21). Right ventricle ratio in animals receiving ETX+either dose of anti-Flt-1 monocolonal antibody was not significantly different from the right ventricle ratio of control animals. Right ventricle ratio in animals receiving ETX+either dose of anti-Flt-1 monocolonal antibody was significantly different from the right ventricle ratio of animals receiving ETX alone. These data indicate that animals given postnatal anti-Flt-1 monoclonal antibody have diminished pulmonary hypertension in an endotoxin induced model of BPD.

Lung Structure

Figure 22:
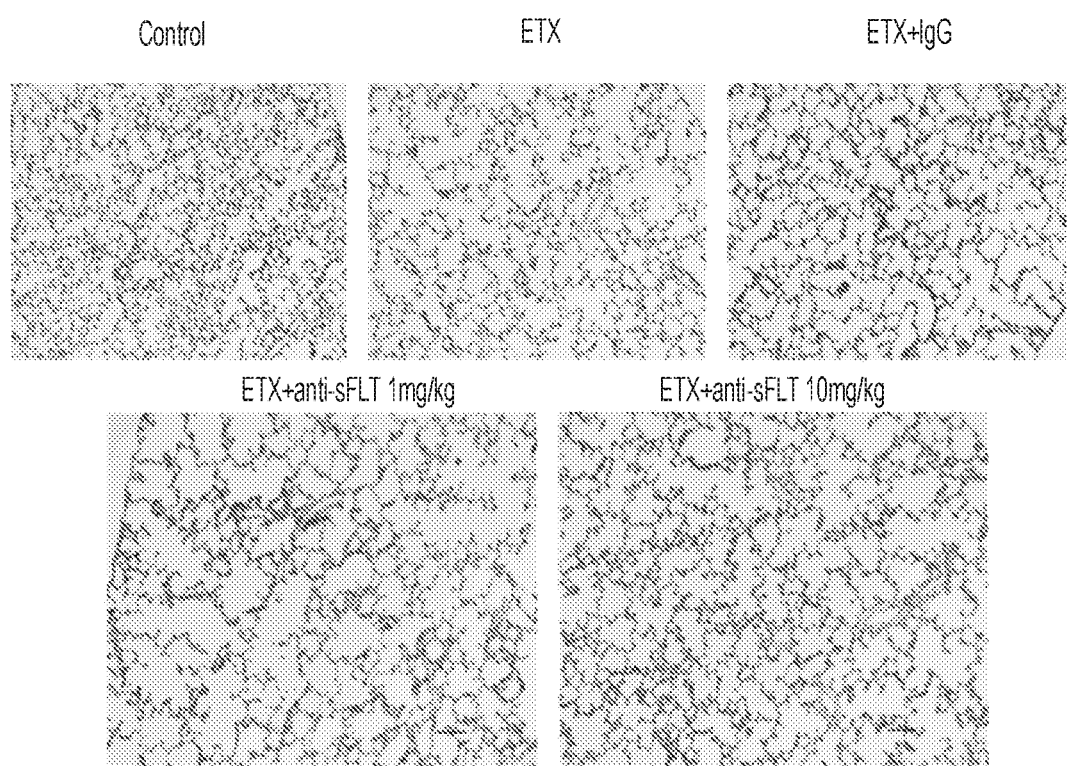
FIG. 22 shows exemplary results illustrating the effects of 1 mg/kg and 10 mg/kg postnatal doses of anti-Flt-1 monoclonal antibody (anti-sFLT) on lung structure in an endotoxin (ETX) induced model of BPD in rats.

Lung structure and pulmonary vessel density was assessed to determine if postnatal anti-Flt-1 monoclonal antibody treatment restored lung structure after antenatal ETX treatment. Lungs of animals administered ETX in utero followed by postnatal treatment with IgG (control treatment) or anti-Flt-1 monoclonal antibody (1 mg/kg or 10 mg/kg) were studied (FIG. 22). These data indicate that postnatal anti-sFlt-1 monoclonal antibody restores lung structure in experimental chorioamnionitis.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

---

We claim:

1. A method of treating bronchopulmonary dysplasia (BPD) in an infant comprising
administering to an infant in need of treatment an effective amount of an anti-Flt-I monoclonal antibody or antigen binding fragment thereof, wherein the administration of the anti-Flt-1 monoclonal antibody or antigen binding fragment thereof results in improved lung development.

2. The method of claim 1, wherein the anti-Flt-1 monoclonal antibody contains a human Fc region.

3. The method of claim 1, wherein the infant is an unborn infant and the anti-Flt-1 monoclonal antibody or antigen binding fragment thereof is administered to the infant via intra-amniotic injection.

4. The method of claim 1, wherein the method comprises parenteral administration to the infant after birth.

5. The method of claim 4, wherein the parenteral administration is an intravenous injection.

6. The method of claim 4, wherein the parenteral administration is an intramuscular injection.

7. The method of claim 4, wherein the parenteral administration is a subcutaneous injection.

8. The method of claim 1, wherein the anti-Flt-1 monoclonal antibody or antigen binding fragment thereof is administered bimonthly, monthly, triweekly, biweekly, weekly, daily, or at variable intervals.

9. The method of claim 1, wherein the anti-Flt-1 monoclonal antibody or antigen binding fragment thereof is delivered to one or more target tissues selected from lungs and heart.

10. The method of claim 1, wherein the effective amount of the anti-Flt-I monoclonal antibody or antigen binding fragment thereof ranges from 0.5 mg/kg body weight to 20 mg/kg body weight per dose.

11. The method of claim 1, wherein the improved lung development comprises growth of healthy lung tissue, decreased lung inflammation, increased alveologenesis, increased angiogenesis, improved structure of pulmonary vascular bed, reduced lung scarring, improved lung growth, reduced respiratory insufficiency, improved exercise tolerance, reduced adverse neurological outcome, or improved pulmonary function.

* * * * *